United States Patent
Khandelwal

(10) Patent No.: US 7,632,520 B2
(45) Date of Patent: Dec. 15, 2009

(54) SYNERGISTIC ANTIBACTERIAL FORMULATION AND TO A METHOD OF MAKING THE SAME

(76) Inventor: Sanjeev Khandelwal, Prem Nivas, 13, Altamount Road, Mumbai 400026 (IN)

( * ) Notice: Subject to any disclaimer, the term of this patent is extended or adjusted under 35 U.S.C. 154(b) by 67 days.

(21) Appl. No.: 11/013,110

(22) Filed: Dec. 15, 2004

(65) Prior Publication Data

US 2005/0181051 A1  Aug. 18, 2005

(30) Foreign Application Priority Data

Feb. 16, 2004 (IN) .......................... 178/MUM/2004
Mar. 3, 2004 (IN) .......................... 258/MUM/2004

(51) Int. Cl.
*A61K 9/20* (2006.01)
*A61K 9/22* (2006.01)
*C12N 1/20* (2006.01)

(52) U.S. Cl. .................. 424/464; 424/468; 424/93.45; 424/93.46; 435/252.9

(58) Field of Classification Search .................. 424/464, 424/468, 93.45, 93.46; 435/252.9
See application file for complete search history.

(56) References Cited

U.S. PATENT DOCUMENTS 6,306,391 B1 * 10/2001 Modi et al. .............. 424/93.44
6,723,358 B1 * 4/2004 van Lengerich .............. 426/94

FOREIGN PATENT DOCUMENTS

JP       01083025       * 3/1989

OTHER PUBLICATIONS

*Lactobacillus sporogenes* (http://www.microbax.com/lactobacillus.htm) p. 1.*

* cited by examiner

*Primary Examiner*—Sreeni Padmanabhan
*Assistant Examiner*—Umamaheswari Ramachandran
(74) *Attorney, Agent, or Firm*—Lucas & Mercanti, LLP

(57) ABSTRACT

A synergistic antibacterial formulation and a method of making the same is disclosed. The composition contains Cefixime Trihydrate+Cloxacillin Sodium+*Lactobacillus sporogenes* spores. The Cloxacillin sodium is in two forms in a sustained release and an immediate release form. A drug delivery system for providing the formulation is provided.

18 Claims, 5 Drawing Sheets

Table 1

Figure 4:
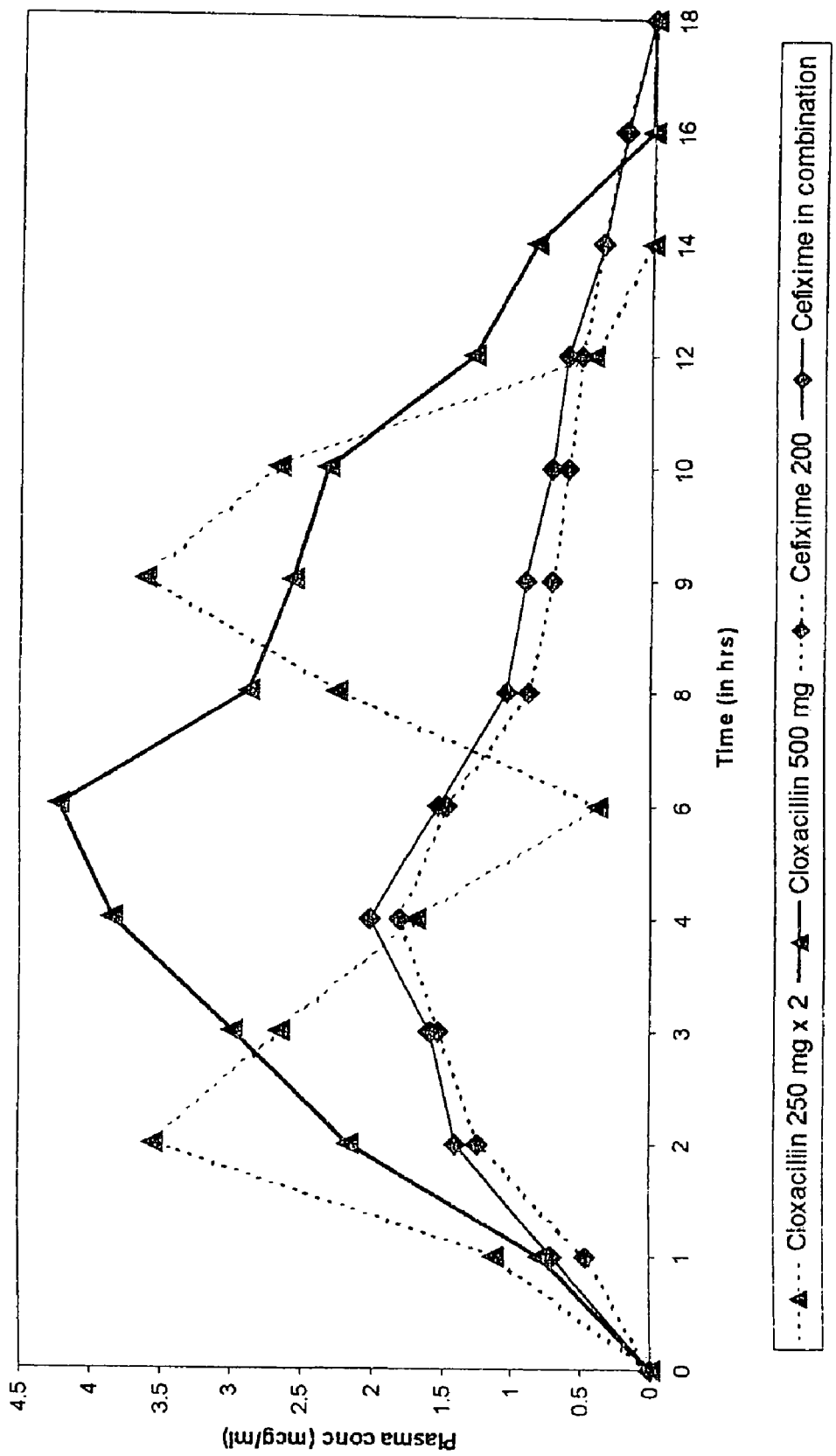

| Organism | MIC$_{90}$ | |
|---|---|---|
| | CEFIXIME | CLOXACILLIN |
| E.coli | 0.25 | |
| K.pnemoniae | 0.01 | |
| P.mirabilis | < 0.06 | |
| C.diversus | 0.12 | |
| Providencia stuartii | 0.12 | |
| Providencia rettgeri | <0.06 | |
| H.influenzae | 0.06 | |
| B.catarrhalis | 0.25 | |
| S.pneumoniae | 0.12 | |
| Salmonella sp. | 0.25 | |
| Shigella sp. | 0.25 | |
| S.aureus | | 0.10 |
| S.epidermidis | | 0.10 |
| Str.pneumoniae | | 0.25 |
| Str.pyogenes | | 0.10 |
| N.gonorrhoeae | | 0.10 |

FIGURE - 1

TABLE – 1A

| PARAMETER | CLOXACILLIN | CEFIXIME |
|---|---|---|
| ORAL ABSORPTION | 40-60% | 50 % |
| Cmax | 8 mg/l | 2 mg/l |
| PLASMA HALF LIFE | 0.5H-0.65 | 3H-0.4 |
| PLASMA PROTEIN BINDING | 93-95% | 60-70% |
| DOSAGE | 250-500 mg QID | 200 mg BID |
| URINARY EXCRETION % | 60-90 | 34-48 |
| CLEARANCE ml/mt/kg | 2.2 + 0.5 | 1.3+0.2 |
| VOL DISTRIBUTION | 0.094 + 0.015 | 0.30 + 0.03 |

FIGURE – 1 A

TABLE 2 A
STABILITY REPORT OF THE TABLET [example 2 batch 1]
(Cefixime + Cloxacillin + L. Sporogenes)

| Cefixime (% age of L.A) | 100.25 | 100.15 | 100.05 | 99.98 |
|---|---|---|---|---|
| Cloxacillin (% age of L.A) | 98.86 | 98.77 | 98.69 | 98.17 |
| *L. Sporogenes* (in million spores) | 93 | 92.68 | 92.36 | 92.15 |

TABLE 2 B
STABILITY REPORT OF THE TABLET [example 2 batch 2]
(Cefixime + Cloxacillin + L. Sporogenes)

| Cefixime (% age of L.A) | 99.88 | 99.68 | 99.65 | 98.84 |
|---|---|---|---|---|
| Cloxacillin (% age of L.A) | 99.38 | 99.12 | 98.82 | 98.23 |
| *L. Sporogenes* (in million spores) | 91 | 90.78 | 90.38 | 90.12 |

TABLE 2 C
STABILITY REPORT OF THE TABLET [example 2 batch 3]
(Cefixime + Cloxacillin + L. Sporogenes)

| Cefixime (% age of L.A) | 99.64 | 99.17 | 99.03 | 98.63 |
|---|---|---|---|---|
| Cloxacillin (% age of L.A) | 99.61 | 99.14 | 99.07 | 98.88 |
| *L. Sporogenes* (in million spores) | 89.83 | 89.61 | 89.37 | 89.12 |

FIGURE - 2

| Time (in hrs) | 0 | 1 | 2 | 3 | 4 | 6 | 8 | 9 | 10 | 12 | 14 | 16 |
|---|---|---|---|---|---|---|---|---|---|---|---|---|
| Cloxacillin 250 mg x 2 | 0 | 1.12 | 3.53 | 2.64 | 1.68 | 0.38 | 2.25 | 3.61 | 2.66 | 0.42 | 0 | 0 |
| Cloxacillin 500 mg | 0 | 0.79 | 2.16 | 2.98 | 3.84 | 4.21 | 2.86 | 2.56 | 2.31 | 1.28 | 0.83 | 0 |
| Cefixime 200 mg | 0 | 0.46 | 1.23 | 1.52 | 1.79 | 1.47 | 0.88 | 0.72 | 0.6 | 0.5 | 0.36 | 0.2 |
| Cefixime in combination | 0 | 0.7 | 1.4 | 1.58 | 2.01 | 1.52 | 1.03 | 0.91 | 0.72 | 0.6 | 0.34 | 0.18 |

FIGURE - 3

SYNERGISTIC ANTIBACTERIAL FORMULATION AND TO A METHOD OF MAKING THE SAME

FIELD OF THE INVENTION

This invention relates to a synergistic antibacterial formulation and to a method of making the same.

WHAT THIS INVENTION ENVISAGES

This invention envisages a composition containing Cefixime Trihydrate+Cloxacillin Sodium+*Lactobacillus sporogenes* spores.

In particular, this invention envisages a drug delivery system for delivering Cefixime Trihydrate U.S.P., Cloxacillin Sodium I.P, and *Lactobacillus sporogenes* spores.

In particular this invention envisages a composition containing Cefixime Trihydrate U.S.P., Cloxacillin Sodium I.P in an extended release oral dosage form and an immediate release form, and *Lactobacillus sporogenes* spores.

BACKGROUND OF THE INVENTION

Cefixime

Cefixime is hygroscopic, slightly soluble in water; sparingly soluble in dehydrated alcohol; practically insoluble in ethyl acetate; freely soluble in methyl alcohol. A 5% suspension in water has a pH of 2.6 to 4.1.

Cefixime is a cephalosporin antibiotic. It is semi-synthetics derived from the secretion of the mold Cephalosporium that can be administered orally and resembles, in respect of its structure, the spectrum of organism fighting ability and the beta-lactamase stability, the 3rd generation cephalosporins of the cefotaxime type, which can be administered parenterally. Third-generation cephalosporins include cefdinir, cefditoren, cefixime, cefoperazone, cefotaxime, cefpodoxime, ceftazidime, ceftibuten, ceftizoxime, and ceftriaxone. The introduction of an acid substituent into the 7 .beta.-side chain of aminothiazolyl-cephalosporins, as, for example, in cefixime, leads to a compound, which can be absorbed enterally. Cefixime is an important molecule to treat wide-ranging infections in a community set up and also as a switch therapy. Cefixime is highly stable to hydrolysis by a wide range of β-Lactamases types 1a, 1b, 1c, 1d, II, III, IV and V.

Like all representatives of this class of substances, it has a bactericidal action. The mechanism of action of cefixime is based on inhibition with the synthesis of the bacterial cell wall—a structure that is not found in eukaryotes. The walls of bacteria are made of a complex polymeric material called peptidoglycan, which contains both amino acids and sugars. Cefixime binds to and inhibits enzymes needed for the synthesis of the peptidoglycan wall. While it has little effect on resting bacteria, it is lethal to dividing bacteria as defective walls cannot protect the organism form bursting in hypotonic surroundings. The acute toxicity of cefixime is negligibly low. Cefixime is stable to hydrolysis by many beta-lactamases.

Cefixime has a mode of action and spectrum of activity similar to that of the third-generation cephalosporin cefotaxime but some Enterobacteriaceae are less susceptible to cefixime. Most third-generation cephalosporins have a high degree of stability in the presence of beta-lactamases (penicillinases and cephalosporinases), and, therefore, have excellent activity against a wide spectrum of gram-negative bacteria, including penicillinase-producing strains of *N. gonorrhoeae* and most Enterobacteriaceae (*Citrobacter, E. coli, Enterobacter, Klebsiella, Morganella, Proteus, Providencia,* and *Serratia* species). However, third-generation cephalosporins in general are susceptible to hydrolysis by chromosomally encoded beta-lactamases. The third-generation cephalosporins are generally not as active against gram-positive cocci as are the first- and second-generation cephalosporins.

Cefixime, has the most activity of all oral cephalosporins against *Streptococcus pyogenes, S. pneumoniae*, and all gram-negative bacilli, including beta-lactamase-producing strains of *H. influenzae, M. catarrhalis*, and *N. gonorrhoeae*. Cefixime has little activity against staphylococci. Cefixime have no activity against *Pseudomonas* species.

Third-generation cephalosporins are used in the treatment of serious gram-negative bacterial infections, including bone and joint infections, female pelvic infections, intra-abdominal infections, gram-negative pneumonia, septicemia, skin and soft tissue infections, including burn wound infections, and complicated urinary tract infections caused by susceptible organisms. Single-dose cefixime has been found to be effective in the treatment of uncomplicated gonorrhea. *Haemophilus influenzae, Moraxella (Branhamella) catarrhalis,* and *Neisseria gonorrhoeae* are sensitive, including penicillinase-producing strains. Of the Gram-positive bacteria, streptococci are sensitive to cefixime but most strains of staphylococci, enterococci, and *Listeria* spp. are not.

Cefixime has therefore bactericidal effects and is effective, for example, for the following pathogens: *Streptococcus pneumoniae, Streptococcus pyogenes, Streptococcus agalactiae; Hamophilus influenzae, Neisseria gonorrhoeae, Escherichia coli, Proteus mirabilis, Proteus vulgaris, Klebsiella pneumoniae, Klebsiella oxytoca, Enterobacter* sp., *Pasteurella multocida, Providencia* sp., *Salmonella* sp., *Shigella* sp., *Citrobacter amalonaticus, Citrobacter diversus, Serratia marcescens*. Cefixime has therefore, excellent activity against a wide variety of Gram –ve organisms and Streptococci (Gram +ve) as given hereunder. But Staphylococci sp. is resistant to Cefixime.

Cefixime-containing compositions are used only in the form of solid dosage forms such as tablets, capsules, granules or powders. Only 40 to 50% of an oral dose of cefixime is absorbed from the gastrointestinal tract, whether taken before or after meals, although the rate of absorption may be decreased in the presence of food. Conventionally, cefixime is better absorbed from oral suspension than from tablets. Absorption is fairly slow. Peak plasma concentrations of 2 to 3 micrograms per mL and 3.7 to 4.6 micrograms per mL have been reported between 2 and 6 hours after single doses of 200 and 400 mg, respectively. The plasma half-life is usually about 3 to 4 hours and may be prolonged when there is renal impairment. About 65% of cefixime in the circulation is bound to plasma proteins. Information on the distribution of cefixime in body tissues and fluids is limited. It crosses the placenta. Relatively high concentrations may be achieved in bile and urine. About 20% of an oral dose (or 50% of an absorbed dose) is excreted unchanged in the urine within 24 hours. Up to 60% may be eliminated by nonrenal mechanisms; there is no evidence of metabolism but some is probably excreted into the faeces from bile. It is not substantially removed by dialysis.

Cefixime is therefore suitable for the treatment of acute and chronic infections of varying severity caused by cefixime-sensitive pathogens and amenable to oral therapy. But cefixime by itself is not suitable for treating infections caused by strains of staphylococci, enterococci, and *Listeria* spp.

Cloxacillin

Cloxacillin on the other hand is an isoxazolyl-penicillin. Cloxacillin sodium is semi synthetic penicillinase-resistant penicillin. It is available commercially as the monohydrate sodium salt, which occurs as an odorless, bitter-tasting, white, crystalline powder. It is freely soluble in water and soluble in alcohol and has a pKa of 2.7. One mg of Cloxacillin sodium contains not less than 825 micrograms of Cloxacillin. Cloxacillin sodium may also be known as sodium Cloxacillin, chlorphenylmethyl isoxazolyl penicillin sodium or methylchlorophenyl isoxazolyl penicillin sodium. Cloxacillin sodium occurs as white or almost white powder that is slightly soluble in water and alcohol. A 1% (10 mg/ml) suspension has a pH from 3-6.5.

Cloxacillin, dicloxacillin and oxacillin have nearly identical spectrums of activity and can be considered therapeutically equivalent when comparing in vitro activity. These penicillinase-resistant penicillins have a narrower spectrum of activity than the natural penicillins. Their antimicrobial efficacy is aimed directly against penicillinase-producing strains of gram-positive cocci, particularly Staphylococcal species. They are sometimes called anti-staphylococcal penicillins. While this class of penicillins also have some activity against some other gram positive and gram-negative aerobes and anaerobes. Cloxacillin is resistant to degradation by penicillinase. Therefore, it is particularly useful against penicillinase-producing staphylococci. Highly active against *Staph. aureus, Strep. pyogenes, Strep. viridians* and *Strep. pneumoniae*.

Cloxacillin is only available in oral dosage forms. Cloxacillin sodium is resistant to acid inactivation in the gut, but is only partially absorbed. The bioavailability after oral administration in humans has been reported to range from 37-60%, and if given with food, both the rate and extent of absorption is decreased. The drug is distributed to the liver, kidneys, bone, bile, pleural fluid, synovial fluid and ascitic fluid. Only minimal amounts are distributed into the CSF, as with the other penicillins. In humans, approximately 90-95% of the drug is bound to plasma proteins. Cloxacillin is partially metabolized to both active and inactive metabolites. These metabolites and the parent compound are rapidly excreted in the urine via both glomerular filtration and tubular secretion mechanisms. A small amount of the drug is also excreted in the feces via biliary elimination. The serum half-life in humans with normal renal function ranges from about 24-48 minutes. Given orally absorption of Cloxacillin is interfered with by food. It reaches high plasma levels in an hour. It is highly concentrated in the kidneys. At the end of a 3-hour i.v. infusion of Cloxacillin 250 mg given to normal subjects, plasma concentrations of the drug was 15 μg/mL. After 2 hours, plasma concentrations were 0.6 μg/mL. Cloxacillin is readily absorbed following i.m. administration and rapidly reaches therapeutically effective blood levels. Serum levels are approximately proportional to dosage. Peak plasma concentrations of 15 μg/mL have been observed 30 minutes after an i.m. injection of Cloxacillin 500 mg; plasma concentrations may be doubled by administration of a doubled dose. Approximately 94% of Cloxacillin binds to circulating plasma proteins, mainly albumin. It is distributed in therapeutic concentrations into the pleural, synovial, bile and amniotic fluids and attains insignificant concentrations in cerebrospinal and ascitic fluids. The plasma half-life of Cloxacillin is between 0.5 and 1.5 hours. Cloxacillin is partially metabolized to microbiologically active and inactive metabolites. Cloxacillin and its metabolites are rapidly excreted in the urine by glomerular filtration and active tubular secretion. The urinary clearance rate was 162.2 mL/minute and a total of 62% of the dose was excreted in the urine in a study of normal subjects receiving an i.v. infusion of 250 mg of Cloxacillin. The drug is also partly eliminated in the feces via biliary excretion. Reduced plasma concentrations of Cloxacillin seen in patients with cystic fibrosis have been attributed to enhanced nonrenal clearance of the drug.

BRIEF DESCRIPTION OF THE ACCOMPANYING DRAWINGS

FIGS. 1 and 1A provide Table 1 in which is tabulated the respective activities of cefixime and Cloxacillin and Table 1A in which are provided the parameters of cefixime and Cloxacillin;

FIG. 2 provides Tables 2A, 2B and 2C in which are tabulated the accelerated Stability study report of different batches of the synergistic formulation in accordance with this invention;

FIG. 3 provides Table 3 in which is tabulated the detailed results of clinical studies conducted for understanding the rationale of the formulation of this invention; and FIG. 4 shows comparative graphs of the studies conducted on the average plasma concentration levels of Cloxacillin and cefixime.

RATIONALE OF PART OF THE INVENTION

Combining Cloxacillin and Cefixime

Therefore it is envisaged in accordance with this invention that a combination of cefixime and Cloxacillin will have additional therapeutic effects. In order to enhance the empiric profile of cefixime which has a narrow spectrum activity, particularly against Gram +ve organisms, such as Staphylococci and Streptococci, the addition of Cloxacillin which provides added impetus to Gram +ve coverage, with MIC90 values as follows: *S. aureus* 0.1 mcg/ml; *S. epidermidis* 0.1 mcg/ml; *Str. pyogenes* 0.1 mcg/ml; *Str. pneumoniae* 0.25 mcg/ml; *N. gonorrheoae* 0.1 mcg/ml converts the combination into a relatively broader spectrum antibiotic.

URTHER BACKGROUND OF THE INVENTION

Unfortunately, the widespread use of antibiotics, especially broad-spectrum antibiotics, has led to deleterious pathological conditions. The physiological health of the gastrointestinal tract is dependent on the health of its microflora. Many individual bacterial species inhabit the gastrointestinal tract and their growth and metabolism depend primarily upon the substrates available to them, most of which are derived from the diet. Administration of antibiotics kills harmful pathogens. But antibiotics do not posses the ability to discriminate between harmful pathogens and beneficial, nonpathogenic microorganisms resident in the flora. These microorganisms, typically the lactic acid producing microorganisms are destroyed by the administered antibiotics, impairing health and digestive function. In the first instance intense diarrhea results. Absorption and assimilation of further dosages of the bioactive ingredients are disturbed and at the same time there may be relapse (the return of infections and their accompanying signs and symptoms).

Modification of the structure and metabolic activity of microflora is achieved through diet, primarily by administering probiotic live microbial food supplements. Different microorganisms prefer different habitats that may differ from host to host species. The best-known probiotics are the lactic acid-producing bacteria (i.e., Lactobacilli) and *Bifidobacte-*

*ria*. Lactobacilli are helpful type of bacteria naturally occurring in the intestines and constitute a major part of intestinal flora. Lactobacilli are indigenous flora colonizing the chicken's crop, the stomach of mice and rats, and the lower ileum in man. Since all probiotics do not permanently colonize the host, they need to be ingested regularly for any health promoting properties to persist. Commercial probiotic preparations generally comprise mixtures of Lactobacilli and *Bifidobacteria*. Different strains of probiotic bacteria may exert different effects based on specific capabilities and enzymatic activities, even within one species. Bacteria colonizing high-transit-rate sites, such as the small intestines, must adhere firmly to the mucosal epithelium and must adapt to the milieu of this adhesion site. The competition for adhesion receptors between probiotic and pathogenic microorganisms, therefore, is dependent on the habitat specifics.

It must be reiterated that most lactic acid-producing or probiotic bacteria however, are extremely sensitive to common antibiotic compounds. More so with a combination of compounds like Cefixime and Cloxacillin envisaged in accordance with this invention. Used without any supportive ingredient such a combination will have lethal effects on the microflora. Accordingly, even during a normal course of individual antibiotic therapy, many individuals develop a number of deleterious physiological side-effects including: diarrhea, intestinal cramping, and sometimes constipation. These side-effects are primarily due to the non-selective action of antibiotics as discussed aforesaid. Thus, individuals taking antibiotics offer suffer from gastrointestinal problems as a result of the beneficial microorganisms (i.e., intestinal flora), which normally colonize the gastrointestinal tract, being killed or severely attenuated. The resulting change in the composition of the intestinal flora can result in vitamin deficiencies when the vitamin-producing intestinal bacteria are killed, diarrhea and dehydration and, more seriously, illness should a pathogenic organism overgrow and replace the remaining beneficial gastrointestinal bacteria. Further, as a result of rapid evacuation of the bowels during diarrhea, a significant amount of the therapeutic compounds also do not get absorbed and are lost in the feces.

Other deleterious results of indiscriminate use of antibiotics is the generation of multiple antibiotic-resistant pathogens and occurrence of secondary opportunistic infections which often result from the depletion of lactic acid producing and other beneficial flora within the gastrointestinal tract. Methicillin-resistant *Staphylococcus aurous* (MRSA) infections and vancomycin-resistant Enterococci (VRE) have been reported. The development of such resistance has led to numerous reports of systemic infections, which are not treatable with conventional antibiotic therapies.

Accordingly, it is envisaged in accordance with this invention that there needs to be added to the Cloxacillin and cefixime combination an artifact in the form of probiotic organisms which functions to militate against the deleterious physiological effects of the antibiotic therapy. These probiotic organisms obviously should be non-pathogenic and non-toxigenic, should retain viability during storage, and should survive passage through the stomach and the small intestine.

The probiotic effects of lactobacilli or lactic acid *bacillus* are well documented. The health claims concerning lactic acid bacteria have been documented in history. In a Persian version of the Old Testament (Genesis 18:8) it states that "Abraham owed his longevity to the consumption of sour milk." In 76 BC the Roman historian Plinius recommended the administration of fermented milk products for treating gastroenteritis. Recently, some investigators, including Metchnikoff, have postulated that the health effects of the lactobacilli to shifts of the intestinal microbial balance. Metchnikoff claimed that the intake of yogurt containing lactobacilli results in a reduction of toxin-producing bacteria in the gut and that this increases the longevity of the host. Tissier, recommended the administration of *Bifidobacteria* to infants suffering from diarrhea, claiming that *Bifidobacteria* supersede the putrefactive bacteria that cause the disease. He showed that *Bifidobacteria* were predominant in the gut flora of breast-fed infants.

Rettger et al and Kopeloff showed that *Lactobacillus acidophilus* may survive in the human gut but the "Bulgarian *bacillus*" did not. Attempts to implant non-lactic acid bacteria such as *Escherichia coli* for "causal fighting against pathological intestinal flora" were undertaken by Nissle in 1916. Bohnhoff et al Freter, and Collins and Carter showed the significant role of the intestinal micro flora for resistance to disease.

The term probiotic, meaning "for life," is derived from the Greek language. It was first used by Lilly and Stillwell in 1965 to describe, "substances secreted by one microorganism which stimulates the growth of another" and thus was contrasted with the term antibiotic. In one particular sense probiotics are microbial-based dietary adjuvant that beneficially affect the host physiology by modulating mucosal & systemic immunity as well as improving nutritional & microbial balance in the intestinal tract [Naidu A S, Bidlack W R, Clemens R A (1999)] In another sense a probiotic is defined as a preparation of or a product containing viable, defined microorganisms with or without other substances in sufficient numbers, which improve or alter the micro flora or their properties (by implantation or colonization) in a compartment of the host and by that exert beneficial health effects in this host." Thus the term can be applied to tissue extracts that stimulate microbial growth. It can also be deemed to mean "organisms and substances which contribute to intestinal microbial balance." Or "A live microbial feed supplement which beneficially affects the host animal by improving its intestinal microbial balance."

The positive effect of lactobacilli on the infection outcome by pathogenic bacteria could be called probiotic only if the effect is achieved beyond implantation of the administrated bacteria or due to a change in the colonizing indigenous micro flora. A direct inhibitory effect exerted by bacteria transiently passing through the gastrointestinal tract fail to meet the criteria. The health effects attributed to the use of probiotics are numerous. The following outcomes are well documented:

Lower frequency and duration of diarrhea associated with antibiotics (*Clostridium dif-ficile*), rotavirus infection, chemotherapy, and, to a lesser extent, traveler's diarrhea;

Stimulation of humoral and cellular immunity;

Decrease in unfavorable metabolites, e.g., ammonium and procancerogenic enzymes in the colon.

There is some evidence of health effects through the use of probiotics for the following:

1) Reduction of *Helicobacter pylori* infection;
2) Reduction of allergic symptoms;
3) Relief from constipation;
4) Relief from irritable bowel syndrome;
5) Beneficial effects on mineral metabolism, particularly bone density and stability;
6) Cancer prevention; and
7) Reduction of cholesterol and triacylglycerol plasma concentrations (weak evidence).

These numerous effects can hardly be explained by a unifying hypothesis that is based on a single quality or mechanism and remains valid for all microorganisms exerting one or the other effect mentioned above. Bacteria are found in much higher numbers in the colon, particularly in the feces, than are lactobacilli. It is self-evident that such microorganisms, which do not necessarily need to adhere to the mucosa, may exert effects bound to this luminal site of action even more efficiently. Moreover, preferences for microhabitats have to be considered. Four microhabitats in the gastrointestinal tract were outlined by Freter as follows: 1) the surface of epitheliums cells; 2) the crypts of the ileum, cecum, and colon; 3) the mucus gel that overlays the epithelium; and 4) the lumen of the intestine. As mentioned above, several indigenous, pathogenic, or probiotic microorganisms target the surface of the epithelium by specific adhesion, often mediated by special organelles, e.g., fimbriae. Motile, spiral-shaped bacteria of the genera *Borellia, Treponema, Spirillium*, and others, e.g., *H. pylori*, typically colonize the crypts. The mucus layer can form a microbial habitat and can protect the host against colonization in some circumstances. As a result of its complex and varying composition and for technical reasons, its function in this context is least clarified.

The luminal content of bacteria depends greatly on bowel transit. Therefore, the microbial density in the small bowel is low, whereas it is abundant in the lumen of the colon, which gives space to microorganisms without adhesion molecules.

When the great variety of species, strain characteristics, and the habitat specifics are considered, it becomes clear that a proven probiotic effect on a one strain or species can not be transferred to other strains or species.

While the gastrointestinal microflora presents a microbial-based barrier to invading organisms, pathogens often become established when the integrity of the microbiota is impaired through stress, illness, antibiotic treatment, changes in diet, or physiological alterations within the G.I. tract such as by commencing a regimen of antibiotics or antibacterials.

Prior Art Disclosure

U.S. Pat. No. 6,306,391 granted to Modi et al discloses a preparation of an oral pharmaceutical formulation containing an anti-infective agent and a microorganism. The formulation suggested in accordance with the said patent contains at least one anti-infective agent and at least one microorganism. The process involves a step of first coating the agent and/or the microorganism to provide a protective barrier around it. Next, the process involves a step of combining the agent and the microorganism into a single pharmaceutical formulation in the form of a capsule or a tablet. The barrier protects the microorganism from the effect of the anti-infective agent to maintain the microorganism in a viable form for a period of at least three months. The agent can be an antibiotic such as amoxycillin. This invention while specifically identifying amoxycillin as the preferred anti-infective agent, indiscriminately lists of other antibiotics including cefixime and Cloxacillin and the microorganism can be *Lactobacillus acidophilus*. Because the use of Lactobacilli in formulations have always been a question mark due to their fragility in the harsh intestinal conditions, the said patent suggests primarily the use of barriers between the antibiotic and the *lactobacillus* and the enteric coating of the formulation to prevent denaturing of the spores in the stomach.

*Lactobacillus acidophilus* in theoretical and controlled experiments consistently exhibits beneficial results to the intestinal tract. However, these results have not been reproduced in practice as a suitable supplement for bacterial replacement. *Lactobacillus acidophilus*, is not stable on the shelf, and many products have no live *lactobacillus* at the point of sale. Also, *Lactobacillus acidophilus* is a bacteria made up of proteins. The stomach's acids break down proteins. Therefore, *Lactobacillus acidophilus*, being protein, is broken down and digested before it is able to reach the intestines. Even if *lactobacillus acidophilus* passes the preliminary stability hurdle, it is killed off in a highly acidic environment of the stomach before it has a chance to reach the small intestine where it is needed. *Lactobacillus Acidophilus* is a producer of D (−) Lactic acid.

Farmer [U.S. Pat. No. 6,461,607] suggested the use of *Lactobacillus Sporogenes*, also known as *Bacillus* coagulans, as an adjuvant to an antibiotic composition. The said patent also suggested the use of spores. The said patent does not, however provide any method of making a tableted formulation embedding the spores or the combination of the spores with a combination of antibiotics.

*Lactobacillus Sporogenes*, is an aerobic to microaerophillic, spore-forming, gram-positive rod, strain of lactic-acid producing *bacillus*, which has many important advantages over *Lactobacillus acidophilus*. It was originally described in 1933. It was isolated in 1949 by Professor Nakayama at Yamanashi University in Japan, in green malt (plant material). *Lactobacillus Sporogenes* naturally occurs in the intestine. It plays a predominant role in intestinal digestion by synthesizing vitamin B3, B5, B6, B12, folic acid, biotin, Vitamin K, bacteriocins and digestive enzymes such as amylase, protease, and lipase. It helps in assimilation of proteins and in digestion of lactose containing dairy products. Unlike other *Lactobacillus* strains, this strain is: Heat resistant Naturally Microencapsulated, Antibiotic and bile acids resistant and Stable at room temperature for 3 years. Based on accelerated stability tests this probiotic can provide up to 95% live lactobacilli after three years storage at room temperature.

*L. Sporogenes* spores have a non-protein shell that protects the bacteria, which remains dormant inside in the shell. *L. Sporogenes*, being in a non-protein shell, can survive the harsh elements that kill "beneficial bacteria": Heat, Light, Oxygen and Acids of the Stomach, to pass through—like roughage—and enter the intestines.

Hence, the spores of *L. sporogenes* are extremely stable, have a long life and are resistant to high temperature, gastric acid and bile acid. It survives gastric acidity and is delivered to the small intestine without loss of viable organisms, in contrast to *L. Acidophilus*, which does not survive well in stomach acid and delivers few living organisms to the small intestine. In the host these spores survive, germinate in the duodenum, proliferate in the small intestine producing abundant lactic acid to prevent proliferation of harmful putrefactive bacteria and create an environment for normal conditioning of the gastrointestinal tract.

The organism requires a complex mixture of organic substrates for growth, including fermentable carbohydrates and peptides. *Lactobacillus sporogenes* does not consume vitamins during its proliferation or growth.

Subsequent to oral administration, therefore, *L. sporogenes* passes through the stomach in its spore form and upon arrival in the duodenum, germinates and multiplies rapidly. Estimates suggest the average duration of time between oral dosing and germination is four hours. (1) After germination, *L. sporogenes* is metabolically active in the intestines, producing lactic acid. *L sporogenes* is considered a semi-resident, indicating it takes up only a temporary residence in the human intestines. Spores of *L. sporogenes* are excreted slowly via the feces for approximately seven days after discontinuation of administration.

Despite the transient nature of this organism in the digestive tract, the changes this lactic acid bacillus produces shift the environment in support of a complex gastrointestinal flora. The mechanism of action is presumed to be a result of improving gastrointestinal ecology by replenishing the quantity of desirable obligate microorganisms and antagonizing pathogenic microbes.

*Lactobacillus* produce two isomeric forms of lactic acid lactic acids, -dextrorotatory-D(−) Lactic acid and laevorotatory L (+) Lactic acid. The L (+) Lactic acid is completely metabolized by the body, leading to glycogen Synthesis, but D (−) Lactic acid is used very slowly by the body and is in fact, never completely metabolized, and excess D (−) Lactic acid can introduce metabolic disturbances, resulting in a degree of metabolic acidosis and may even be toxic to the brain. *L. sporogenes* produces only L(+) lactic acid. *L. sporogenes* is assumed to produce bacteriocins and short chain fatty acids. As the organism grows, it assimilates and incorporates cholesterol into its cellular structure. *L. sporogenes* possesses significant [beta]-galactosidase (lactase) activity in vitro.

In laboratory animals with bacterial dysbiosis, *L. sporogenes* supplementation inhibits growth of pathogenic microorganisms and results in renewal of desirable obligate gastrointestinal organisms to normal levels. Reports suggest that supplementation produces a rapid resolution of acute gastrointestinal infection induced by pathogenic bacteria in calves. It has been reported that the efficacy of treatment in patients with bacterial dysbiosis receiving *L sporogenes* was 20-30 percent higher than traditional probiotics such as *Lactobacillus acidophilus* or *Bifidobacteria*.

Clinical studies have revealed that *L. sporogenes* can be successfully implanted in the intestine. *L. sporogenes* satisfies the essential requirements of an efficient probiotic. Preparations of *L. sporogenes* in pharmaceutical dosage forms such as tablets, capsules, dried granules or powder have the following characteristics:

- They contain a large number of viable lactobacilli that retain viability during preparation in pharmaceutical dosage forms and during storage before consumption. The spores are thermo stable as against viable *L. acidophilus* cells, which may not withstand lyophilization.
- Survive in gastric secretions and bile of the upper digestive tract and reach the intestine safely. Settle in the digestive tract and produce enough lactic acid and other antagonistic substances to inhibit the growth of pathogenic bacteria.
- Being sporulated, they germinate under favorable conditions and produce sufficient viable cells, which proliferate and perform vital healthful functions as described earlier.
- In addition, *L. sporogenes* spores are semi-resident and are slowly excreted out of the body 7 days after discontinuation of administration.

*Lactobacillus sporogenes* spores are therefore capable of providing protection from pathogenic invasions into intestinal tract and help to restore the normal balance of the intestinal flora without any pathological or pharmacological side effects.

Due to its spore-forming nature, it survives manufacturing, shipping and storage with no loss of viable organisms, and unlike *L. Acidophilus*, needs no special handling, such as freezing or refrigeration.

Rationale for the Formulation of Invention

Therefore the formulation of this invention logically includes *Lactobacillus sporogenes* spores as an integral and active part of the formulation along with Cloxacillin sodium and cefixime trihydrate.

An object of this invention is to provide an antibiotic formulation which has broad spectrum effective activity as described hereinabove and which does not disturb the intestinal flora but on the contrary restores the flora even during administration of the formulation.

The broad spectrum activity can be achieved by combining cefixime and Cloxacillin in a single dosage formulation. However, this posed a particular problem. Cefixime and Cloxacillin require to be administered differently because of their significantly different plasma half lives and plasma-protein binding activity.

After a drug enters the systemic circulation, it is distributed to the body's tissues. The entry rate of a drug into a tissue depends on various factors such as the rate of blood flow to the tissue and tissue mass. A drug is uniquely distributed in the body. Some drugs go into fat, others remain in the ECF, and still others are bound avidly to specific tissues, commonly liver or kidney. The volume of fluid into which a drug appears to be distributed or diluted is called the apparent volume of distribution (the fluid volume required to contain the drug in the body at the same concentration as in plasma). This parameter provides a reference for the plasma concentration expected for a given dose and for the dose required to produce a given concentration. Drugs such as Cloxacillin are highly protein-bound and thus have a small apparent volume of distribution. The extent of drug distribution into tissues depends on the extent of plasma protein and tissue binding. Drugs are transported in the bloodstream partly in solution as free (unbound) drug and partly bound to blood components (eg, plasma proteins, blood cells). The ratio of bound to unbound drug in plasma is mainly determined by the reversible interaction between a drug and the plasma protein to which it binds, as governed by the law of mass action. Many plasma proteins such as Albumin can interact with drugs. The crystal structure of albumin has three homologous structural domains (domains I, II, and III), which contain two drug binding sites: Drug binding site 1 is located in domains I and II, and drug binding site 2 is located in domain III. Only unbound drug is thought to be available for passive diffusion to extra-vascular or tissue sites where pharmacological effects occur. Therefore, the unbound drug concentration may be more closely related to drug concentration at the active site and to drug effects, often making the fraction unbound (ratio of unbound to total concentrations) a more useful parameter than the fraction bound. Plasma protein binding influences distribution and the apparent relationship between pharmacologic activity and total plasma drug concentration.

The conventional dosage unit on oral administration exhibits first order kinetics i.e. transient increase in plasma drug concentration to a peak followed by exponential decay. The magnitude of plasma drug concentration is influenced by dose administration and the interval and rate of drug ADME. An ideal dosage form should be capable of delivering a known amount of drug to a specific site in the body at a predetermined rate or combination of rates in order to produce the optimum therapeutic effect. The half life or t ½ is the time taken for the plasma concentration of a drug in the body to be reduced by 50 percent. The removal or elimination of a drug takes place both through excretion and drug metabolism and is not linear with time. Therefore drugs can linger in the body for a significant time period. For example if a drug has a half-life of 1 h then 1 h would be 25% of the original dose left and after 3 h, 12.5% would remain. Therefore it would take 7 h for the level of that drug to fall below 1% of the original dose. Some drugs such as Cloxacillin have short half lives (38 min) whereas others such as cefixime have longer half-life measures is 3 hours with a little variation over the usual therapeutic dosage range of 200 to 400 mg doses as a single or two divided doses.

As greater analytical sensitivity has been achieved, it has been found that lower concentration appear to yield longer and longer terminal half-lives. Thus it has been appreciated that half-life is a derived parameter that changes as a function of both clearance and volume of distribution. Because drugs start to be metabolized and eliminated as soon as they are administered it is necessary to provide regular doses in order to maintain therapeutic levels in the body. Therefore it is important to know that half-life of the drug in order to calculate the frequency of dosing required to reach and maintain these levels. In general the time taken to reach a steady-state concentration is six times the drug's half-life. For example the concentration level of half-life of 4 hours supplied at 4-hourly intervals is as follows:

| Time of dosing (h) | Max level (ug/ml) | Min level (ug/ml) |
|---|---|---|
| 0 | 1.0 | 0.5 |
| 4 | 1.5 | 0.75 |
| 8 | 1.75 | 0.87 |
| 12 | 1.87 | 0.94 |
| 16 | 1.94 | 0.97 |
| 20 | 1.97 | 0.98 |
| 24 | 1.98 | 0.99 |

Further, the concept of clearance is extremely useful in clinical pharmacokinetics because clearance of a given drug usually is constant over the range of concentration encountered clinically. This true because systems for elimination of drugs usually are not saturated and thus absolute rate of elimination of the drug is essentially a linear functions of its concentration in plasma synonymous statement is at the elimination of most drugs follows first order kinetics—a constant fraction of drug is eliminated per unit of time.

There is a fluctuation in concentration level in the between each dose. The level is at a maximum after each dose and falls to a minimum before the next dose is administered. It is important to ensure that the level dose not drop below the therapeutic level but does not rise to such a level the side effects are induced. The time taken to reach steady state concentration is not dependent on the size of the dose but the concentration level of drug in the blood achieved at steady state is. Therefore the final dose level at steady state concentration depends on the size of each dose given as well as the frequency of the doses.

During clinical trials blood samples are taken from patients at regular intervals to determine the concentration of the drug in the blood. This will help determine the proper dosing regime in order to get the ideal concentration of drug in the blood. The clinician usually wants to maintain steady state concentration of a drug within a known therapeutic range (maxim being the amount of dug that may cause toxics side effects and minimum being the amount of drug needed to produce the desirable effect in the body.

Assuming complete bioavailability the steady state will be achieved when the rate of drug elimination equals the rate of drug administration.

Dosing rate=$CL.C_{SS}$

Where CL is clearance and $C_{SS}$ is steady state concentration of drug. Thus if the desired steady state concentration of drug in plasma or blood is known the rate of clearance of drug by the patient will dictate the rate at which the drug should be administered. Half life is therefore a derived parameter that changes as a function of both clearance and volume of distribution of drug in the body. Half life provides a good indication of the time required to reach steady state after a dosage regimen is initiated. Typically four half lives are required for 94 percent of a new steady state. It is also a good indicator for the time for a drug to be removed from the body and a means to estimate the appropriate dosing interval. It has been found that the plot of log plasma concentration versus time is linear and the rate of decline is constant logarithmically.

Another crucial parameter is the plasma protein binding activity which is 93 to 95% in the case of Cloxacillin whereas it is only 60 to 70% in the case of Cefixime. Administered separately, Cloxacillin is generally administered QID, i.e. every four hours or four times a day in dosages ranging from 250 to 500 mg, whereas Cefixime is administered BID i.e. twice a day every twelve hours in a typical dosage of 200 mg to 400 mg. Again Cloxacillin should be given at least 30 minutes before meals as presence of food in the stomach reduces the drug absorption. These significant different rate and range of dosage have hitherto militated against the combined use of Cloxacillin and cefixime in a combined formulation.

Statement of the Invention

According to this invention there is provided a synergistic antibiotic formulation comprising (i) a core consisting of Cloxacillin sodium 30 to 75% of the mass of the formulation, of which 60 to 90% is in a sustained release matrix containing Hydroxypropylmethyl cellulose and a binder, the remaining Cloxacillin sodium being in an immediate release intimate mixture together with cefixime trihydrate, 15 to 40% of the total mass of Cloxacillin sodium; *lactobacillus sporogenes* being 0.5 to 4% of the total mass of the Cloxacillin sodium; and excipients including lubricants 1 to 5% mass of the Cloxacillin sodium and disintegrants being 1 to 5% of the mass of the Cloxacillin sodium and a (ii) coating enveloping the core said coating consisting of a coating polymer having mass 1 to 3% of the mass of the core; a solvent for dissolving the polymer having a mass of 5 to 45% of the mass of the core; a plasticizer having a mass of 0.05 to 2% of the mass of the core; and a coloring-agent having a mass of 0.05 to 2% of the mass of the core.

Rationale for Use of HPMC Matrix

Hydroxypropyl methylcellulose [HPMC] is a methylcellulose modified with a small amount of propylene glycol ether groups attached to the anhydroglucose of the cellulose. The dry product contains 19 percent. to 30 percent. of methoxyl (—OCH3) groups and 3 percent. to 12 percent. of hydroxypropyl (—OCH2CHOHCH3) groups. The hydroxypropylmethyl cellulose selected for making of the matrix in accordance with this invention has a viscosity ranging from 3000 cps to 120,000 cps and its mass is 3 to 15% of the total mass of the Cloxacillin sodium. The particle size throughput efficiency of HPMC is above 98.5% in 100 mesh, and 100% in 80 mesh. Its carbonization temperature: 280-300 Celsius and apparent density: 0.25-0.70 g·cm3 (usually about 0.5 g/cm3), specific gravity: 1.26-1.31. HPMC has a surface tension: 42-56 dyn/cn (2% aqueous solution). It is soluble in water and some organic solvents. The solubility varies with the viscosity, the lower the viscosity, higher is its solubility. HPMCs of different viscosities have different properties and solubilities in water at different pH. The lower methoxyl content in HPMC, the higher gelation temperature, the lower solubility in water and surface activity. hydroxypropyl methylcellulose. Use of HPMC, has been widely studied for its application in oral Sustained Release systems since the early 1960s. HPMC has also other characteristic such as thickening property, pH stability, water retention, excellent film-forming property and good disperse and adhesion power.

HPMC displays good compression properties, can accommodate high levels of drug loading, and is considered non-toxic. When in contact with water, HPMC hydrates rapidly and forms a gelatinous barrier layer around the tablet. The underlying mechanisms of drug release from these systems are complex, involving up to three moving boundaries, usually termed the swelling, diffusion, and erosion fronts. The rate of drug release from HPMC matrix is dependent on various factors, such as type of polymer, drug, polymer/drug ratio, particle size of drug and polymer, and the type and amount of fillers used in the formulation. Therefore predetermined quantities of HPMC of different viscosities ranging from 3000 to 15,000 cps have been selected for the making of the matrix of this invention for embedding the sustained release component of Cloxacillin sodium.

Rationale for Use of Other Excipients

Excipients play a unique functional role in formulation design of a Sustained release tablet. Apart from HPMC, the release-rate controlling polymer, other excipients utilized in the fabrication of a hydrophilic matrix are fillers, binders, lubricants, glidants, etc. These materials are often necessary to enhance tablet formulation properties (to improve lubricity, powder flow, and compressibility) or to modify the drug-release profile. The effect of fillers on HPMC matrix performance will be dependent on the drug substance, the polymer level, and the level of the filler itself. Drug release from HPMC matrices is found to be affected by applied compression force. At all compression forces the binder used, particularly the starch type binders, effect the drug release. The use of a binder renders tablets extremely poor in self-disintegrating properties. Thus when Starch is used, drug release is significantly slower compared to formulations containing microcrystalline cellulose or lactose. Partially pre-gelatinized maize starch contributes to retardation of release. This effect is imparted through synergistic interactions between the binder such as Starch and HPMC and the filler actively forming an integral part within the HPMC gel structure. Disintegrants are therefore used and are an integral part of the formulation of the invention.

The matrix in accordance with this invention includes a binder and the mass of the binder is typically 1 to 6% of the total mass of the Cloxacillin sodium. Particularly, the binder is selected which would not give adverse effects on the self-disintegrating properties of tablets The preferred binder is at least one binder selected from a group containing acacia, sodium alginate, starch, gelatin, pregelatinized starch, partly pregelatinized starch, saccharides, including glucose, sucrose, dextrose and lactose, molasses, extract of Irish moss, panwar gum, guar gum, ghatti gum, mucilage of isapol husk, carboxy methylcellulose, methylcellulose, veegur, larch arabolactan, polyethylene glycols, ethylcellulose, alcohols, waxes, and polyvinylpyrrolidone, hydroxypropylcellulose, preferably low-viscosity type (L-type) hydroxypropylcellulose, hydroxy-propylmethylcellulose, starch, gum arabic, dextrin, pullulan and the like. Among these binders, polyvinylpyrrolidone, hydroxypropylcellulose and are more preferred, and Hydroxypropylmethyl cellulose of viscosity cps is the most preferred. When these binders are used in an amount of 1 to 6% by mass of the total mass of Cloxacillin sodium, preferably 2 to 3.5% by mass, on a per-tablet basis, tablets which can self-disintegrate rapidly can be produced by a conventional production method.

The matrix includes a solvent and the mass of the solvent in the matrix is 15 to 40% of the mass of the Cloxacillin sodium in the matrix. Typical solvents include Dichloromethane, other halogenated hydrocarbons (e.g. dichloroethane, etc.), Iso propyl alcohol, other alcohols such as methanol, ethanol, etc.), Acetone, other ketones (e.g. methyl ethyl ketone, etc.), adiponitrile, propylene glycol, N,N-dimethylformamide, N,N-dimethylacetamide, dimethyl sulphoxide and N-methyl-2-pyrrolidone, acetonitrile, lower aliphatic alcohols (straight or branched chain), acetone, 2-butanone, tetrahydrofuran, dimethylformamide, dimethylsulphoxide, ethers (e.g. diethyl ether, tetrahydrofuran, dioxane, etc.), hydrocarbons (e.g. hexane, heptane, benzene, toluene, etc.), aprotic polar solvents (e.g. dimethylformamide, dimethyl sulfoxide, etc.), which may be used alone or combination of two or more thereof.

The core of the synergistic antibiotic formulation includes a lubricant which is at least one compound selected from a group of compounds which include can be added to the composition to reduce adhesion and ease release of the product. Lubricants include, but are not limited to, magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, surfactants, talc, waxes and zinc stearate.

Another preferred aspect of the invention comprises the incorporation of at least one disintegrating agent in the formulation in accordance with this invention. Such an agent, which will accelerate the dispersion of the active particles. Examples of disintegrating agents according to the invention include cross-linked polyvinylpyrrolidone, carboxymethyl starch, natural starch, microcrystalline cellulose, cellulose gum and mixtures of these. A preferred content of disintegrating agent is from 1% to 5% of the total mass of the Cloxacillin sodium.

The synergistic antibiotic formulation preferably includes at least one surfactant selected from the group consisting of: sodium lauryl sulfate, sodium carboxy methyl cellulose, calcium carboxy methyl cellulose, hydrogenated or non-hydrogenated glycerolipids, ethoxylated or non-ethoxylated, linear or branched, saturated or mono- or polyunsaturated $C_6$ to $C_{30}$ fatty acids in the form of the acid or an alkali metal or its salt, cyclodextrin, sodium lauryl sulfate, alkaline earth metal or amine salt, ethoxylated or non-ethoxylated esters of sucrose, sorbitol, sorbitan monooleate, mannitol, glycerol or polyglycerol containing from 2 to 20 glycerol units, or glycol with said fatty acids, mono-, di- or triglycerides or mixtures of glycerides of said fatty acids, ethoxylated or non-ethoxlylated, linear or branched, saturated or mono- or polyunsaturated ($C_6$ to $C_{30}$ fatty alcohols, cholesterol and derivatives thereof, other derivatives with a sterol skeleton, ethoxylated or non-ethoxylated ethers of sucrose, sorbitol, mannitol, glycerol or polyglycerol containing from 2 to 20 glycerol units, or glycol with said fatty alcohols, hydrogenated or non-hydrogenated, polyethoxylated vegetable oils, polyoxyethylene/polyoxypropylene block polymers (poloxamers), polyethylene glycol hydroxystearate, sphingolipids and sphingosine derivatives, polyalkyl glucosides, ceramides, polyethylene glycol/alkyl glycol copolymers, and polyethylene glycol/polyalkylene glycol ether di-block or tri-block copolymers, diacetylated monoglycerides, diethylene glycol monostearate, ethylene glycol monostearate, glyceryl monooleate, glyceryl monostearate, propylene glycol monostearate, macrogol esters, macrogol stearate 400, macrogol stearate 2000, polyoxyethylene 50 stearate, macrogol ethers, cetomacrogol 1000, lauromacrogols, nonoxinols, octoxinols, tyloxapol, poloxamers, polyvinyl alcohols, polysorbate 20, polysorbate 40, polysorbate 60, polysorbate 65, polysorbate 80, polysorbate 85, sorbitan monolaurate, sorbitan monooleate, sorbitan monopalmitate, sorbitan monostearate, sorbitan sesquioleate, sorbitan trioleate, sorbitan tristearate and sucrose esters.

In use it has been surprising discovered that the use of the formulation has a synergistic effect. On testing the plasma concentrations of both drugs it has been found that the plasma concentrations of both drugs are significantly higher. A probable explanation for this synergistic effect is that both Cefexime and Cloxacillin when co-administered compete with the same sites on the plasma protein, particularly albumin and 1 alpha glyco protein, both being acidic in pH, are attached to the same binding site 1 in the albumin. Both drugs have therefore have reduced plasma binding, as a result greater quantity of the active free drug is available, consequently the plasma concentration is higher. More so in the case of Cloxacillin, with the result that significantly the same therapeutic effect is achieved by administering the formulation of this invention twice a day [two doses of 500 mg each]. Therapeutic effects are achieved with half the conventional dose of Cloxacillin [2 grams divided in doses of 500 mg each].

The process for making the composition in accordance with this invention is as follows:

The process involves making a core by
1. mixing together Cloxacillin sodium 20 to 65% of the mass of the formulation, Hydroxy propyl methylcellulose 3 to 15% of the mass of the Cloxacillin sodium, a binder 1 to 6% of the mass of the Cloxacillin sodium and a solvent 15 to 45% of the mass of the Cloxacillin sodium, at speeds of 15 to 50 rpm to produce a sustained release homogenous mass;
2. milling the homogenous mass through mesh sizes ranging from 8 to 18 mm to obtain milled wet sustained release core particles;
3. drying the milled core particles without heating for 10 to 20 minutes to obtain partially dried sustained release core particles;
4. drying the partially dried sustained release core particles at temperatures ranging between 45 to 60 degrees Celsius for 30 to 60 minutes to obtain unsized dried sustained release core particles having moisture not more than 4%;
5. sifting and milling the dried core particles through mesh sizes ranging from 12 to 20 mesh to obtain sized dried sustained release core particles containing Cloxacillin sodium;
6. vibrosifting together through a sifter having mesh size ranging from 30 to 40 mesh Cloxacillin sodium 10 to 35% of the mass of the total formulation; together with cefixime trihydrate 15 to 40% of the mass of Cloxacillin sodium; *lactobacillus sporogenes* being 0.5 to 4% mass of the Cloxacillin sodium; disintegrants being 1 to 5% of the mass of the Cloxacillin sodium to obtain vibrosifted immediate release particles;
7. mixing together the sized dried sustained release core particles and the vibrosifted immediate release particles at temperatures below 25 degrees Celsius; at a relative humidity of less than 60 percent for 20 to 30 minutes at 20 to 500 rpm;
8. adding to the mixture excipients including lubricants 1 to 5% mass of the Cloxacillin sodium and further mixing for 3 to 5 minutes to obtain core particles;
9. compressing the core particles at temperatures below 25 degrees Celsius; at a relative humidity of less than 60 percent at compression pressures ranging from 1 kg/sq cm to 12 kg/sq cm in dies having cavities of predetermined dimensions to obtain cores of the antibiotic formulation;

and enveloping the said cores with a coating consisting of a coating polymer having mass 1 to 3% of the mass of the core; a solvent for dissolving the polymer having a mass of 5 to 45% of the mass of the core; a plasticizer having a mass of 0.05 to 2% of the mass of the core; and a coloring agent having a mass of 0.05 to 2% of the mass of the core in a coating machine at temperatures ranging from 40 to 60 degrees Celsius to obtain the synergistic antibiotic formulation.

Process in Detail:

Step 1: making of the matrix which contains primarily the extended or sustained release Cloxacillin sodium:

A predetermined quantity of Cloxacillin sodium of particle size ranging from to mesh is sifted and sieved and placed in a mixer, typically a planetary mixer along with a predetermined quantities of hydroxypropyl methyl cellulose of viscosities ranging between 3000 cps and 120,000 cps sifted and sieved particles of size ranging from to mesh. The ambient temperature is maintained below 25 degrees Celsius and the relative humidity below 60%. The mass of the Cloxacillin sodium selected is 60 to 90 percent of the total mass of Cloxacillin sodium intended in the final formulation.

The mixer is then run for 20 to 30 minutes between 15 to 50 r.p.m. so that a homogenous mixture of the particles of Cloxacillin sodium and the HPMC results.

A predetermined quantity of a binder which is 1 to 6% of the mass of the total mass of Cloxacillin sodium is selected and added to a solvent whose mass is 15 to 40% of the mass of the Cloxacillin sodium selected for the matrix. The solvent and binder are added into an inert container such as of stainless steel under continuous stirring until a clear solution is formed and the binder is completely dissolved in the solvent. The solution is then added to the planetary mixer containing the homogenous mixture of the particles of Cloxacillin sodium and the HPMC.

Wet mixing is then commenced for 15 to 50 minutes at 15 to 50 r.p.m. to obtain a wet homogenous mixture mass. Additional solvent may be added during the mixing process.

The wet homogenous mixture mass is milled, typically in a multimill fitted with 10 mm perforated sieve with medium speed (knives) to obtain granules of mesh size 8 to 18 mm.

The wet granules are subjected to a two stage drying: In the first stage the granules are subjected to ambient conditioning at 25 to 30 degrees Celsius so that the solvent dries out by evaporation; In the second stage the conditioned granules are subjected to temperate heated drying at temperatures between 45 to 60 degrees Celsius in a tray drier or a fluidized bed drier for 30 to 60 minutes. The drying mass is continuously raked during the process. The Loss on drying should not be more than 4%.

The dry granules are sifted and milled, typically in a multimill to obtain dry sustained release granules of Cloxacillin sodium of mesh size 12 to 20 mesh.

Step 2: making the core containing the sustained release granules of Cloxacillin sodium, cefixime trihydrate immediate release Cloxacillin sodium and lactobacillus sporogenes spores:

Through a vibro sifter of mesh size 30 to 40 mesh is passed:

Pre determined quantity of Cloxacillin sodium particles, being the balance remaining quantity of the total mass of Cloxacillin sodium;

Pre determined quantity of Cefixime trihydrate particles, being 15 to 50% by mass of the total mass of Cloxacillin sodium;

Pre determined quantity of lactobacillus sporogenes spores, being 0.5 to 4% by mass of the total mass of Cloxacillin sodium;

Pre determined quantity of disintegrants, being 1 to 5% by mass of the total mass of Cloxacillin sodium;

Pre determined quantity of glidant, being 0 to 6% by mass of the total mass of Cloxacillin sodium; [optional]. Glidants are added to improve the flow properties of the formulation and improve the accuracy of dosing. Excipients that may function as glidants include, but are not limited to, colloidal silicon dioxide, magnesium trisilicate, powdered cellulose, starch, talc and tribasic calcium phosphate, Pre determined quantity of surfactant, being 0 to 5% by mass of the total mass of Cloxacillin sodium; [optional]

This sifted mass along with the dried sustained release granules of Cloxacillin sodium granules are transferred to a double cone blender at temperatures below 25 degrees Celsius and the mass is blended at speeds of 20 to 50 r.p.m. for 20 to 30 minutes.

Pre determined quantity of sifted lubricants, being 1 to 5% by mass of the total mass of Cloxacillin sodium, is then added to the blender and further blending is done for 3 to 5 minutes resulting in the lubricated core mass. This core mass is fed to hopper of a compression machine, typically a rotary compression machine and the compression pressure is set at 2 kg/sq cm to 12 kg/sq cm. Preferred compression pressure is 6 to 8 kg/sq cm.

Applied pressure influence drug-release rate, which is dependent on the type of filler used. An increase in compression force results in slower drug release. The compression force, by changing the dimensions of inter-particulate voids, modifies the drug-release kinetics. These voids govern both the rate of penetration of fluid into the tablet matrix and the release of the dissolved drug.

Cores are obtained.

Step 3 coating of the cores:

The cores are coated with a film coating. A coating suspension is pre prepared by mixing together a coating polymer 1 to 3% mass of the core together with a solvent 5 to 45% of the mass of the core; a plasticizer 0.05% to 2% of the mass of the core and a coloring agent 0.05 to 1% of the mass of the core in a s.s. container and stirred for five minutes using overhead stirrer until a smooth slurry is obtained. The coating solution is sieved typically through a 80 mesh sieve.

Many polymers require high processing temperature and they may decompose at this temperature but on addition on plasticizers have very good heat resistance to prevent discoloration or decomposition of the polymeric materials.

1. Plasticizers increase the flexibility of the polymeric material.
2. Some plasticizers impart good low temperature performance.
3. Polymeric plasticizers increase the life of the end products considerably.
4. Plasticizers give the good weather resistance.
5. Plasticizers improve chemical resistances.

The de-dusted cores are transferred into a coating pan and the tablet bed is heated by inching process using hot air blower. The initial temperature should not exceed 45-50° C. Once the tablet bed attains 45° C. it is ready for spray coating with the coating suspension. The tablets are coated with coating suspension. Special environmental conditions are necessary for the coating. These are temperature between 20 to 27 degrees C. and relative humidity below 60%.

EXAMPLES

Example 1

50.0 Kg of Cloxacillin sodium and 6.0 Kg of HPMC of average viscosity 4000 cps [sustained release grade] were passed through a 30-mesh sieve and placed in a planetary mixer. The ambient temperature was maintained below 25 degrees Celsius and the relative humidity below 60%. The mixer was run for 25 minutes at 30 r.p.m. so that a homogenous mixture of the particles of Cloxacillin sodium and the HPMC resulted.

800 gms of HPMC of Average viscosity 50 cps was mixed with 8.0 Kg of Dichloromethane and 12.0 Kg of isopropyl alcohol in a stainless steel [s.s.] tank under continuous stirring until a clear solution was formed and the binder was completely dissolved in the solvent. The solution was then added to the planetary mixer containing the homogenous mixture of the particles of Cloxacillin sodium and the HPMC.

et mixing was then commenced for 20 minutes at 15 r.p.m. to obtain a wet homogenous mixture mass.

The wet homogenous mixture mass was milled, in a multimill fitted with 12 mm perforated sieve to obtain granules of mesh size 8 to 12 mm.

The wet granules were subjected to a two stage drying:

In the first stage the granules were subjected to ambient conditioning at 25 degrees Celsius for 20 minutes so that the solvent dried out;

In the second stage the conditioned granules were subjected to heated drying at a temperature of 50 degrees Celsius in a tray drier for 60 minutes. The drying mass was raked during the process. The Loss on drying was 3%.

The dry granules were sifted in an 18 mesh vibrosifter to obtain dry sustained release granules of Cloxacillin sodium of mesh size 12 to 18 mesh.

Step 2: making the core containing the sustained release granules of Cloxacillin sodium, cefixime trihydrate immediate release Cloxacillin sodium and *lactobacillus sporogenes* spores:

Through a vibro sifter of mesh size 40 mesh were passed:

7.6 Kg of Cloxacillin sodium particles, being the balance remaining quantity of the total mass of Cloxacillin sodium; 11.2 Kg of Cefixime trihydrate particles, 750 gm of *lactobacillus sporogenes* spores, 1.0 kg sodium starch glycollate, 0.3 kg of colloidal silicon dioxide; 1.0 kg of sodium lauryl sulfate and 1.0 kg of talc.

This sifted mass along with the dried sustained release granules of Cloxacillin sodium granules were transferred to a double cone blender at temperature of 22 degrees Celsius and the mass was blended at speed of 30 r.p.m. for 25 minutes.

1.0 kg of magnesium stearate; was then added to the blender and further blending was done for 5 minutes resulting in the lubricated core mass. This core mass was fed to hopper of a single rotary compression machine and the compression pressure was set at 6 kg/sq cm.

1,00,000+ Cores were obtained:

Dimension:

Length—19.0±0.2 mm

Width—8.0±0.2 mm

Thickness—5.2±0.3 mm

Average weight of core 806.2 mg±3%.

The cores were coated with a film coating.

A coating suspension was pre prepared by mixing together 0.8 kg of ethyl cellulose; and 0.8 kg of hydroxypropyl cellulose and mixed together with 12 kg of isopropyl alcohol and 22 kg of Methylene chloride; 0.01 kg of diethyl phthalate, 0.15 kg of titanium dioxide in a s.s. container and stirred for five minutes using overhead stirrer until a smooth slurry was obtained. The coating solution was sieved through a 80 mesh sieve.

The de-dusted cores were transferred into a coating pan and the tablet bed was heated by inching process using hot air blower. The initial temperature was set at 40° C. Once the tablet bed attains 45° C. it was ready for spray coating with the coating suspension. The cores were coated with the coating suspension. The relative humidity was maintained below 60% throughout. The coated tablets were polished with talc.

Final dimensions of the tablets were as follows:

Dimension:

Length—19.1±0.2 mm

Width—8.1±0.2 mm

Thickness—5.3±0.3 mm

Average weight of film coated tablet 820 mg±3%. Each tablet contained:

Cloxacillin sodium equivalent to Cloxacillin: 250 mg sustained release

Cloxacillin sodium equivalent to Cloxacillin: 250 mg immediate release

Cefixime trihydrate equivalent to Cefixime: 100 gms immediate release; and

*Lactobacillus sporogenes* spores 45 million spores.

Example 2

40.0 Kg of Cloxacillin sodium and 3.0 Kg of HPMC of Average viscosity 4000 cps, and 2.0 kg of HPMC Average viscosity 1,00,000 cps [sustained release grade] were passed through a 30 mesh sieve and placed in a planetary mixer. The ambient temperature was maintained below 25 degrees Celsius and the relative humidity below 60%.

The mixer was run for 25 minutes at 40 r.p.m. so that a homogenous mixture of the particles of Cloxacillin sodium and the HPMC resulted.

500 gms of ethyl cellulose was mixed with 10.0 Kg of isopropyl alcohol and 0.01 kg of propylene glycol in a stainless steel [s.s.] tank under continuous stirring until a clear solution was formed and the binder was completely dissolved in the solvent. The solution was then added to the planetary mixer containing the homogenous mixture of the particles of Cloxacillin sodium and the HPMC.

Wet mixing was then commenced for 25 minutes at 35 r.p.m. to obtain a wet homogenous mixture mass.

The wet homogenous mixture mass was milled, in a multimill fitted with 12 mm perforated sieve to obtain granules of mesh size 8 to 12 mm.

The wet granules were subjected to a two stage drying:

In the first stage the granules were subjected to ambient conditioning at 20 degrees Celsius for 30 minutes so that the solvent dried out;

In the second stage the conditioned granules were subjected to heated drying at a temperature of 45 degrees Celsius in a fluidized bed drier for 50 minutes. The drying mass was raked during the process. Loss on drying was 2.4%.

The dry granules were sifted in an 18-mesh vibrosifter to obtain dry sustained release granules of Cloxacillin sodium of mesh size 12 to 18 mesh.

Step 2: making the core containing the sustained release granules of Cloxacillin sodium, cefixime trihydrate immediate release Cloxacillin sodium and *lactobacillus sporogenes* spores:

Through a vibro sifter of mesh size 40 mesh were passed: 17.6 Kg of Cloxacillin sodium particles, being the balance remaining quantity of the total mass of Cloxacillin sodium; 22.4 Kg of Cefixime trihydrate particles, 1.5 gm of *lactobacillus sporogenes* spores, 1.0 kg sodium carboxy methyl cellulose [surfactant], 1.0 kg of microcrystalline cellulose; and 1.0 kg of corn starch.

This sifted mass along with the dried sustained release granules of Cloxacillin sodium granules were transferred to a double cone blender at temperature of 20 degrees Celsius and the mass was blended at speed of 40 r.p.m. for 30 minutes.

1 kg of purified stearic acid; was then added to the blender and further blending was done for 5 minutes resulting in the lubricated core mass. This core mass was fed to hopper of a single rotary compression machine and the compression pressure was set at 8 kg/sq cm.

1,00,000+ Cores were obtained:

Dimension:

Length—19.0±0.2 mm

Width—8.0±0.2 mm

Thickness—6.4±0.3 mm

Average weight of core 910.1 mg±3%.

The cores were coated with a film coating.

A coating suspension was pre prepared by mixing together 1.0 kg of hydroxypropyl cellulose; and 1.0 kg of ethyl cellulose and mixed together with 16 kg of isopropyl alcohol and 24 kg of Methylene chloride; 0.01 kg of polyethylene glycol, 0.15 kg of titanium dioxide and 0.05 kg of iron oxide yellow coloring agent in a s.s. container and stirred for fifteen minutes using overhead stirrer until a smooth slurry was obtained. The coating solution was sieved through a 80 mesh sieve.

The de-dusted cores were transferred into a coating pan and the tablet bed was heated by inching process using hot air blower. The initial temperature was set at 40° C. Once the tablet bed attained 45° C. it was ready for spray coating with the coating suspension. The cores were coated with the coating suspension. The relative humidity was maintained below 60% throughout. The coated tablets were polished with talc.

Dimension:

Length—19.1±0.2 mm

Width—8.1±0.2 mm

Thickness—6.4±0.3 mm

Average weight of film coated 930 mg±3%.

Each tablet contained:

Cloxacillin sodium equivalent to Cloxacillin: 250 mg sustained release

Cloxacillin sodium equivalent to Cloxacillin: 250 mg immediate release

Cefixime trihydrate equivalent to Cefixime: 200 gms immediate release;

And *Lactobacillus sporogenes* spores 90 million spores.

Example 3

50.0 Kg of Cloxacillin sodium and 6.0 Kg of HPMC of Average viscosity 4000 cps [sustained release grade] were passed through a 30-mesh sieve and placed in a planetary mixer. The ambient temperature was maintained below 25 degrees Celsius and the relative humidity below 60%. The mixer was run for 25 minutes at 40 r.p.m. so that a homogenous mixture of the particles of Cloxacillin sodium and the HPMC resulted. 800 gms of HPMC of Average viscosity 50 cps was mixed with 12 Kg of isopropyl alcohol andh8 kg of methylene chloride in a stainless steel [s.s.] tank under continuous stirring until a clear solution was formed and the binder was completely dissolved in the solvent. The solution was then added to the planetary mixer containing the homogenous mixture of the particles of Cloxacillin sodium and the HPMC.

Wet mixing was then commenced for 25 minutes at 35 r.p.m. to obtain a wet homogenous mixture mass.

The wet homogenous mixture mass was milled, in a multimill fitted with 12 mm perforated sieve to obtain granules of mesh size 8 to 12 mm.

The wet granules were subjected to a two stage drying:

In the first stage the granules were subjected to ambient conditioning at 30 degrees Celsius for 30 minutes so that the solvent dried out;

In the second stage the conditioned granules were subjected to heated drying at a temperature of 45 degrees Celsius in a fluidized bed drier for 50 minutes. The drying mass was raked during the process.

The Loss on drying was 2%.

The dry granules were sifted in an 18-mesh vibrosifter to obtain dry sustained release granules of Cloxacillin sodium of mesh size 12 to 18 mesh.

Step 2: making the core containing the sustained release granules of Cloxacillin sodium, cefixime trihydrate immediate release Cloxacillin sodium and *lactobacillus sporogenes* spores:

Through a vibro sifter of mesh size 40 mesh were passed: 7.6 Kg of Cloxacillin sodium particles, being the balance remaining quantity of the total mass of Cloxacillin sodium; 22.4 Kg of Cefixime trihydrate particles, 1.5 gm of *lactobacillus sporogenes* spores, 1.0 kg sodium starch glycolate, 0.3 kg of colloidal silicon dioxide; 1.0 kg of talc and 1.0 kg of sodium lauryl sulphate [surfactant].

This sifted mass along with the dried sustained release granules of Cloxacillin sodium granules were transferred to a double cone blender at temperature of 20 degrees Celsius and the mass was blended at speed of 40 r.p.m. for 30 minutes.

1 kg of magnesium stearate; was then added to the blender and further blending was done for 5 minutes resulting in the lubricated core mass. This core mass was fed to hopper of a single rotary compression machine and the compression pressure was set at 10 kg/sq cm.

1,00,000 Cores were obtained

Dimension:

Length—19.0±0.2 mm

Width—8.0±0.2 mm

Thickness—6.2±0.3 mm

Average weight of core 926 mg±3%.

The cores were coated with a film coating.

A coating suspension was pre prepared by mixing together 1.0 kg of HPMC of viscosity 6 cps; and 1.0 kg of ethyl cellulose and mixed together with 14.0 kg of isopropyl alcohol and 22.0 kg of Methylene chloride; 0.01 kg of diethyl phthalate, 0.2 kg of titanium dioxide in a s.s. container and stirred for five minutes using overhead stirrer until a smooth slurry was obtained. The coating solution was sieved through a 80 mesh sieve.

The de-dusted cores were transferred into a coating pan and the tablet bed was heated by inching process using hot air blower. The initial temperature was set at 40° C. Once the tablet bed attained 45° C. it was ready for spray coating with the coating suspension. The cores were coated with the coating suspension. The relative humidity was maintained below 60% throughout. The coated tablets were polished with talc.

Dimension:

Length—19.1±0.2 mm

Width—8.1±0.2 mm

Thickness—6.3±0.3 mm

Average weight of film coated 946 mg±3%.

Each tablet contained:

Cloxacillin sodium equivalent to Cloxacillin: 250 mg sustained release

Cloxacillin sodium equivalent to Cloxacillin: 250 mg immediate release

Cefixime trihydrate equivalent to Cefixime: 200 gms immediate release;

And *Lactobacillus sporogenes* spores 90 million spores.

Example 4

40 Kg of Cloxacillin sodium and 2.5 Kg of HPMC of Average viscosity 4000 cps [sustained release grade], 2.5 kg of HPMC of Average viscosity 15000 cps were passed through a 30 mesh sieve and placed in a planetary mixer. The ambient temperature was maintained below 25 degrees Celsius and the relative humidity below 60%.

The mixer was run for 25 minutes at 40 r.p.m. so that a homogenous mixture of the particles of Cloxacillin sodium and the HPMC resulted.

500 gms of ethyl cellulose was mixed with 12 Kg of isopropyl alcohol in a stainless steel [s.s.] tank under continuous stirring until a clear solution was formed and the binder was completely dissolved in the solvent. The solution was then added to the planetary mixer containing the homogenous mixture of the particles of Cloxacillin sodium and the HPMC.

Wet mixing was then commenced for 25 minutes at 35 r.p.m. to obtain a wet homogenous mixture mass.

The wet homogenous mixture mass was milled, in a multimill fitted with 12 mm perforated sieve to obtain granules of mesh size 8 to 12 mm.

The wet granules were subjected to a two stage drying: In the first stage the granules were subjected to ambient conditioning at 20 degrees Celsius for 30 minutes so that the solvent dried out;

In the second stage the conditioned granules were subjected to heated drying at a temperature of 45 degrees Celsius in a fluidized bed drier for 50 minutes. The drying mass was raked during the process.

The loss on drying was 2.5%.

The dry granules were sifted in an 18-mesh vibrosifter to obtain dry sustained release granules of Cloxacillin sodium of mesh size 12 to 18 mesh.

Step 2: making the core containing the sustained release granules of Cloxacillin sodium, cefixime trihydrate immediate release Cloxacillin sodium and *lactobacillus sporogenes* spores:

Through a vibro sifter of mesh size 40 mesh were passed:

17.6 Kg of Cloxacillin sodium particles, being the balance remaining quantity of the total mass of Cloxacillin sodium;

22.4 Kg of Cefixime trihydrate particles, 1.5 gm of *lactobacillus sporogenes* spores, 1.0 kg of microcrystalline, 1.0 kg of talcum and 1.0 kg of sodium lauryl sulphate [surfactant]. This sifted mass along with the dried sustained release granules of Cloxacillin sodium granules were transferred to a double cone blender at temperature of 20 degrees Celsius and the mass were blended at speed of 40 r.p.m. for 30 minutes.

1 kg of calcium stearate was then added to the blender and further blending was done for 5 minutes resulting in the lubricated core mass. This core mass was fed to hopper of a single rotary compression machine and the compression pressure was set at 8 kg/sq cm.

1,00,000 Cores were obtained:

Dimension:

Length—19.0±0.2 mm

Width—8.0±0.2 mm

Thickness—6.2±0.3 mm

Average weight of the core tablet—923.1 mg±3%.

The cores were coated with a film coating.

A coating suspension was pre prepared by mixing together 2 kg of cellulose acetate pthalate of 0.01 kg of propylenene glycol and mixed together with 14 kg of isopropyl alcohol, 24 kg methylene chloride, 0.15 kg of titanium dioxide and 0.050 erythrose coloring agent in a s.s. container and stirred for five minutes using overhead stirrer until a smooth slurry was obtained. The coating solution was sieved through a 80 mesh sieve.

The de-dusted cores were transferred into a coating pan and the tablet bed was heated by inching process using hot air blower. The initial temperature was set at 40° C. Once the tablet bed attained 45° C. it was ready for spray coating with the coating suspension. The cores were coated with the coating suspension. The relative humidity was maintained below 60% throughout. The coated tablets were polished with talc.

Dimension:

Length—19.1±0.2 mm

Width—8.1±0.2 mm

Thickness—6.3±0.3 mm

Average weight of the film coated tablet—943.00 mg±3%.

Final dimensions of the tablets were as follows:

Each tablet contained:

Cloxacillin sodium equivalent to Cloxacillin: 250 mg sustained release

Cloxacillin sodium equivalent to Cloxacillin: 250 mg immediate release

Cefixime trihydrate equivalent to Cefixime: 200 gms immediate release;

And *Lactobacillus sporogenes* spores 90 million spores.

Example 5

45.00 Kg of Cloxacillin sodium and 5.0 Kg of HPMC of Average viscosity 1,000,00 cps [sustained release grade] were passed through a 30 mesh sieve and placed in a planetary mixer. The ambient temperature was maintained below 25 degrees Celsius and the relative humidity below 60%. The mixer was run for 25 minutes at 40 r.p.m so that a homogenous mixture of the particles of Cloxacillin sodium and the HPMC resulted. 1 kg of hydroxy propyl cellulose was mixed with 10 Kg of isopropyl alcohol in a stainless steel [s.s.] tank under continuous stirring until a clear solution was formed and the binder was completely dissolved in the solvent. The solution was then added to the planetary mixer containing the homogenous mixture of the particles of Cloxacillin sodium and the HPMC.

Wet mixing was then commenced for 25 minutes at 35 r.p.m. to obtain a wet homogenous mixture mass.

The wet homogenous mixture mass was milled, in a multimill fitted with 12 mm perforated sieve to obtain granules of mesh size 8 to 12 mm.

The wet granules were subjected to a two stage drying:

In the first stage the granules were subjected to ambient conditioning at 30 degrees Celsius for 20 minutes so that the solvent dried out;

In the second stage the conditioned granules were subjected to heated drying at a temperature of 45 degrees Celsius in a fluidized bed drier for 50 minutes. The drying mass was raked during the process. The Loss on drying was 2.3%.

The dry granules were sifted in an 18-mesh vibrosifter to obtain dry sustained release granules of Cloxacillin sodium of mesh size 12 to 18 mesh.

Step 2: making the core containing the sustained release granules of Cloxacillin sodium, cefixime trihydrate immediate release Cloxacillin sodium and *lactobacillus sporogenes* spores:

Through a vibro sifter of mesh size 40 mesh were passed:

12.6 Kg of Cloxacillin sodium particles, being the balance remaining quantity of the total mass of Cloxacillin sodium; 22.4 Kg of Cefixime trihydrate particles, 1.5 gm of *lactobacillus sporogenes* spores, 1.0 kg pregelatinised starch, 0.8 kg of sodium lauryl sulfate [surfactant], 1.0 kg of talc.

This sifted mass along with the dried sustained release granules of Cloxacillin sodium granules were transferred to a double cone blender at temperature of 20 degrees Celsius and the mass were blended at speed of 40 r.p.m. for 30 minutes.

1 kg of calcium stearate; was then added to the blender and further blending was done for 5 minutes resulting in the lubricated core mass. This core mass was fed to hopper of a single rotary compression machine and the compression pressure was set at 8 kg/sq cm.

1,00,000 Cores were obtained

Average wt. of the core tablet 918.1 mg

Average wt. of the film coated tablet 938 mg

Dimension:

Length 19.0±0.2 mm

Width 8.0±0.2 mm

Thickness 6.2 mm±0.3 mm

The cores were coated with a film coating.

A coating suspension was pre prepared by mixing together 0.6 kg of HPMC of Average viscosity 6 cps; and 0.6 kg of hydroxypropyl cellulose and mixed together with 15 kg of isopropyl alcohol and 24 kg of Methylene chloride; 0.01 kg of polyethylene glycol, 0.15 kg titanium dioxide and 0.06 kg of quinoline yellow coloring agent in a s.s. container and stirred for fifteen minutes using overhead stirrer until a smooth slurry was obtained. The coating solution was sieved through 80-mesh sieve.

The de-dusted cores were transferred into a coating pan and the tablet bed was heated by inching process using hot air blower. The initial temperature was set at 40° C. Once the tablet bed attained 45° C. it was ready for spray coating with the coating suspension. The cores were coated with the coating suspension. The relative humidity was maintained below 60% throughout. The coated tablets were polished with talc.

Final dimensions of the tablets were as follows:
Average wt. of the film coated tablet 938 mg
Dimension:

Length 19.1±0.2 mm

Width 8.1±0.2 mm

Thickness 6.3 mm±0.3 mm
Each tablet contained:

Cloxacillin sodium equivalent to Cloxacillin: 250 mg sustained release

Cloxacillin sodium equivalent to Cloxacillin: 250 mg immediate release

Cefixime trihydrate equivalent to Cefixime: 200 mg immediate release;

*Lactobacillus sporogenes* spores 90 million spores.

Example 6

45.00 Kg of Cloxacillin sodium and 5.0 Kg of HPMC of Average viscosity 1,000,00 cps [sustained release grade] were passed through a 30-mesh sieve and placed in a planetary mixer. The ambient temperature was maintained below 25 degrees Celsius and the relative humidity below 60%. The mixer was run for 25 minutes at 40 r.p.m so that a homogenous mixture of the particles of Cloxacillin sodium and the HPMC resulted. 1 kg of hydroxy propyl cellulose, 0.01 kg of polysorbate 80 was mixed with 10 Kg of isopropyl alcohol in a stainless steel [s.s.] tank under continuous stirring until a clear solution was formed and the binder was completely dissolved in the solvent. The solution was then added to the planetary mixer containing the homogenous mixture of the particles of Cloxacillin sodium and the HPMC.

Wet mixing was then commenced for 25 minutes at 35 r.p.m. to obtain a wet homogenous mixture mass.

The wet homogenous mixture mass was milled, in a multimill fitted with 12 nun perforated sieve to obtain granules of mesh size 8 to 12 mm.

The wet granules were subjected to a two stage drying:

In the first stage the granules were subjected to ambient conditioning at 30 degrees Celsius for 20 minutes so that the solvent dried out;

In the second stage the conditioned granules were subjected to heated drying at a temperature of 45 degrees Celsius in a fluidized bed drier for 50 minutes. The drying mass was raked during the process. The Loss on drying was 2.3%.

The dry granules were sifted in an 18-mesh vibrosifter to obtain dry sustained release granules of Cloxacillin sodium of mesh size 12 to 18 mesh. Step 2: making the core containing the sustained release granules of Cloxacillin sodium, cefixime trihydrate immediate release Cloxacillin sodium and *lactobacillus sporogenes* spores:

Through a vibro sifter of mesh size 40 mesh were passed:
12.6 Kg of Cloxacillin sodium particles, being the balance remaining quantity of the total mass of Cloxacillin sodium; 11.2 Kg of Cefixime trihydrate particles, 0.75 kgs of *lactobacillus sporogenes* spores, 1.2 kg microcrystalline cellulose, 0.3 kgs colloidal silicon dioxide, 0.8 kg of sodium lauryl sulfate [surfactant] and 1.0 kg of talc.

This sifted mass along with the dried sustained release granules of Cloxacillin sodium granules were transferred to a double cone blender at temperature of 20 degrees Celsius and the mass were blended at speed of 40 r.p.m. for 30 minutes.

1 kg of calcium stearate; was then added to the blender and further blending was done for 5 minutes resulting in the lubricated core mass. This core mass was fed to hopper of a single rotary compression machine and the compression pressure was set at 8 kg/sq cm.

1,00,000 Cores were obtained:
Average wt. of the core tablet 798.6 mg
Dimension:

Length 19.0±0.2 mm

Width 8.0±0.2 mm

Thickness 5.2 mm±0.3 mm
The cores were coated with a film coating.

A coating suspension was pre prepared by mixing together 0.4 kg of HPMC of Average viscosity 6 cps; and 0.4 kg of hydroxypropyl cellulose, 0.8 kg of ethyl cellulose and mixed together with 12 kg of isopropyl alcohol and 22 kg of Methylene chloride; 0.01 kg of polyethylene glycol, 0.15 kg titanium dioxide and 0.06 kg of quinoline yellow coloring agent in a s.s. container and stirred for fifteen minutes using overhead stirrer until a smooth slurry was obtained. The coating solution was sieved through 80-mesh sieve.

The de-dusted cores were transferred into a coating pan and the tablet bed was heated by inching process using hot air blower. The initial temperature was set at 40° C. Once the tablet bed attained 45° C. it was ready for spray coating with the coating suspension. The cores were coated with the coating suspension. The relative humidity was maintained below 60% throughout. The coated tablets were polished with talc.

Final dimensions of the tablets were as follows:

Average wt. of the core tablet 816 mg

Dimension:

Length 19.1±0.2 mm

Width 8.1±0.2 mm

Thickness 5.3 mm±0.3 mm
Each tablet contained:

Cloxacillin sodium equivalent to Cloxacillin: 250 mg sustained release

Cloxacillin sodium equivalent to Cloxacillin: 250 mg immediate release

Cefixime trihydrate equivalent to Cefixime: 100 mg immediate release;

*Lactobacillus sporogenes* spores 45 million spores.

Example 7

20.0 Kg of Cloxacillin sodium and 2.5 Kg of HPMC of Average viscosity 4000 cps, 2.5 Kg of HPMC of Average viscosity 15,000 cps [sustained release grade] were passed through a 30-mesh sieve and placed in a planetary mixer. The ambient temperature was maintained below 25 degrees Celsius and the relative humidity below 60%.

The mixer was run for 25 minutes at 40 r.p.m so that a homogenous mixture of the particles of Cloxacillin sodium and the HPMC resulted. 0.5 kg of ethyl cellulose, 0.01 kg of polyethylene glycol 4000, 0.3 kg of povidone was mixed with 8 Kg of isopropyl alcohol in a stainless steel [s.s.] tank under continuous stirring until a clear solution was formed and the binder was completely dissolved in the solvent. The solution was then added to the planetary mixer containing the homogenous mixture of the particles of Cloxacillin sodium and the HPMC.

Wet mixing was then commenced for 25 minutes at 35 r.p.m. to obtain a wet homogenous mixture mass.

The wet homogenous mixture mass was milled, in a multimill fitted with 12 mm perforated sieve to obtain granules of mesh size 8 to 12 mm.

The wet granules were subjected to a two stage drying:

In the first stage the granules were subjected to ambient conditioning at 30 degrees Celsius for 20 minutes so that the solvent dried out In the second stage the conditioned granules were subjected to heated drying at a temperature of 45 degrees Celsius in a fluidized bed drier for 50 minutes. The drying mass was raked during the process. The Loss on drying was 2.3%.

The dry granules were sifted in an 18-mesh vibrosifter to obtain dry sustained release granules of Cloxacillin sodium of mesh size 12 to 18 mesh.

Step 2: making the core containing the sustained release granules of Cloxacillin sodium, cefixime trihydrate immediate release Cloxacillin sodium and *lactobacillus sporogenes* spores:

Through a vibro sifter of mesh size 40 mesh were passed:

8.8 Kg of Cloxacillin sodium particles, being the balance remaining quantity of the total mass of Cloxacillin sodium; 11.2 Kg of Cefixime trihydrate particles, 0.5 kgs of *lactobacillus sporogenes* spores, 1.0 kg microcrystalline cellulose, 10.0 kg of sodium lauryl sulfate [surfactant] and 1.0 kg of talc.

This sifted mass along with the dried sustained release granules of Cloxacillin sodium granules were transferred to a double cone blender at temperature of 20 degrees Celsius and the mass were blended at speed of 40 r.p.m. for 30 minutes.

1 kg of calcium stearate; was then added to the blender and further blending was done for 5 minutes resulting in the lubricated core mass. This core mass was fed to hopper of a single rotary compression machine and the compression pressure was set at 8 kg/sq cm.

1,00,000+ Cores were obtained:

Average wt. of the core tablet 503.1 mg

Dimension:

Length 14.0±0.2 mm

Width 8.0±0.2 mm

Thickness 5.0 mm±0.3 mm

The cores were coated with a film coating.

A coating suspension was pre prepared by mixing together 1.2 kg of cellulose acetate phthalate and propylene glycol mixed together with 8 kg of isopropyl alcohol and 16 kg of Methylene chloride; 0.01 kg of polyethylene glycol, 0.08 kg titanium dioxide and 0.04 kg of erythrosine coloring agent in a s.s. container and stirred for fifteen minutes using overhead stirrer until a smooth slurry was obtained. The coating solution was sieved through 80-mesh sieve.

The de-dusted cores were transferred into a coating pan and the tablet bed was heated by inching process using hot air blower. The initial temperature was set at 40° C. Once the tablet bed attained 45° C. it was ready for spray coating with the coating suspension. The cores were coated with the coating suspension. The relative humidity was maintained below 60% throughout. The coated tablets were polished with talc.

Final dimensions of the tablets were as follows:

Average wt. of the core tablet 514 mg

Dimension:

Length 14.1±0.2 mm

Width 8.1±0.2 mm

Thickness 5.3 mm±0.3 mm

Each tablet contained: Cloxacillin sodium equivalent to Cloxacillin: 125 mg sustained release Cloxacillin sodium equivalent to Cloxacillin: 125 mg immediate release Cefixime trihydrate equivalent to Cefixime: 100 mg immediate release; *Lactobacillus sporogenes* spores 30 million spores.

In accordance with another embodiment of the invention a flavonoid is added to the immediate release cefixime trihydrate. Typical flavonoids include quercetin, genistein, naringin, diosmin, acacetin and chrysin which are added at step of core making. The flavonoids enhance the absorption of the drug in the GI tract.

Example 8

In the process of example 3, in the step 2 of making the core, 25 grams of quercetin was added at the time of adding the cefixime trihydrate, preferably at the time of sifting so that the flavonoids is well dispersed throughout the mass of cefixime. Rest of the process was the same as in example 3.

Normal storage conditions did not generally affect drug release. All tablets had low weight variation and good mechanical strength initially and after 6 months accelerated temperature storage. Application of film coatings generally resulted in an increase in tablet breaking force initially and on storage. Good stability results were produced at all storage conditions after 1, 2, 3, 6, and 12 months. No changes were observed in tablet appearance. No significant decrease in tablet mechanical strength was recorded. Dissolution profiles were compared The results indicated that no significant difference was observed in drug release rates after 12 months storage at all storage conditions for both Cloxacillin and cefixime.

Tablets of example 3 different batches were studied for stability. The accelerated Stability study report found in table 2 shown in FIG. 2 of the accompanying drawings of the formulation of example 3 different batches suggest that there is no significant decrease of the Count of the *Lactobacillus Sporogenes* found even after three months in the accelerated temperature which may be equivalent to 24 months room temperature storage. This further suggests that the formulation in accordance with this invention is a stable formulation at least for a period of 18 months in the normal room temperature storage.

Clincal Trials

Clinical Trial 1

Tablets of example 2 were subjected to clinical trials conducted at St. George's Hospital, Mumbai on 500 patients to assess the Efficacy and Safety of the tablets in Upper/Lower Respiratory Tract Infections, Skin & Soft Tissue Infection and Post surgical wounds. This was an open, multicentric, non-comparative study.

Inclusion Criteria:

Male/female patients' between 18-65 years

History and findings suggestive of URTI or LRTI

Skin and Soft Tissue Infections

Post-surgical wounds

Exclusion Criteria:

Hypersensitivity to any of the drugs in this combination

Hepatic and Renal impairment

Pregnant/Lactating women

On antibiotic therapy in the last 15 days

| RESULTS | CLINICAL OUTCOME |
| --- | --- |
| Cure | 61.3% |
| Improvement | 35.7% |
| Clinical success | 97.0% |
| (Cure + Improvement) | |
| Bacteriological outcome | |
| Eradication | 93.4% |
| Failure | 6.6% |

None of the patients who were part of the clinical trials complained of diarrhea or any other symptoms of antibiotic administration.

Stools of several patients were tested for detection of *lactobacillus* count even after five days of administration. The *lactobacillus* count was found within normal range in all cases. This compares favourably with the finding that *lactobacillus* count significantly drops after antibiotic administration.

Clinical Trial 2

Comparative studies were conducted on 24 healthy male patients who were pre-tested for non-allergic conditions against Betalactam and Cephalsporin antibiotics. In the first stage the volunteers were co-administered two 250 mg of Cloxacillin after 6 hour intervals and one 200 mg of Cefixime in separate tablet form and blood plasma conc was noted for every one for 16 hours. After 5 days the same set of 24 patients were administered the synergetic formulation in accordance with this invention and similar plasma conc. was noted every one hour. The table-3 in FIG. 3 of accompanying drawing gives the detailed results and the average of the 24 is plotted. FIG. 4 of the accompanying drawings shows a graph of the studies conducted on the average plasma concentration levels of Cloxacillin and cefixime. This is contrasted with the graphs of Cloxacillin and cefixime concentrations in representative medications of the prior art.

The graph illustrates the synergetic effect of the formulation. The single dose of cloxacillin provided significantly better plasma concentration much better than two dosages of the cloxacillin. Significantly even the cefixime shows better conc. (competitive effect)

Out of 24 patients, 7 patients who were given the conventional dose, had mild diarrhea, dyspepsia and discomfort in the abdomen. One patient had acute diarrhea other patients did not reveal any symptoms. On administration of the formulation of this invention none of the volunteers exhibited any gastric symptoms including diarrhea.

The invention claimed is:

1. An antibiotic formulation comprising (i) a core containing Cloxacillin sodium, cefixime trihydrate, *lactobacillus sporogenes* ant at least one pharmaceutically acceptable excipient said core coated with at least one layer of a polymeric coat;

said core comprising a sustained release part and an immediate release part;

said sustained release part comprising cloxacillin sodium incorporated in a hydroxypropyl methyl cellulose matrix and optionally a binder;

said immediate release part comprises an intimate mixture of (i) cloxacillin sodium, (ii) cefixime trihydrate, (iii) *lactobacillus sporogenes*, (iv) a lubricant, and (v) optionally a disintegrant;

said polymeric coat consisting of (i) a coating polymer in amount about 1 to 3% by mass of the core, (ii) a solvent for dissolving the polymer in amount about 5 to 45% by mass of the core, (iii) a plasticizer in amount about 0.05 to 2% by mass of the core, and (iv) a coloring agent in amount about 0.05 to 2% by mass of the core; wherein (i) the total amount of cloxacillin sodium is about 48.63 to 61.27% by mass of the total formulation, (ii) about 60 to 90% of total cloxacillin sodium in the formulation is present in the sustained release part, the remaining being in the immediate release part, (iii) the amount of cefixime trihydrate in the immediate release part is about 20 to 40% by mass of the total cloxacillin sodium in the formulation and (iv) the amount of *lactobacillus sporogenes* in the immediate release part is about 0.5 to 4% by mass of the total cloxacillin sodium in the formulation.

2. The antibiotic formulation of claim 1, in which the hydroxypropyl methyl cellulose has viscosity ranging from 3,000 cps to 120,000 cps.

3. The antibiotic formulation of claim 1, in which the mass of hydroxypropyl methyl cellulose in the sustained release part is 3 to 15% of the mass of the total Cloxacillin sodium in the formulation.

4. The antibiotic formulation of claim 1, in which the amount of the binder is about 1 to 6% of the mass of the total Cloxacillin sodium in the formulation.

5. The antibiotic formulation of claim 1, in which the excipient is a solvent in an amount of about 15 to 40% by mass of the total Cloxacillin sodium in the formulation.

6. The antibiotic formulation of claim 1, in which the solvent is at least one member selected from the group consisting of dichloromethane, acetone, adiponitrile, propylene glycol, N,N-dimethylformamide, N,N-dimethylacetamide, dimethylsulphoxide and N-methyl-2-pyrrolidone, acetonitrile, lower aliphatic alcohols (straight or branched chain), acetone, 2-butanone, tetrahydrofuran, dimethylsulphoxide, lower alcohols, ethers, hydrocarbons, halogenated hydrocarbons, ketones, aprotic polar solvents.

7. The antibiotic formulation of claim 1, in which the disintegrant is at least one compound selected from the group consisting of starch, days, cellulose derivatives, gums, algins, combinations of hydrocarbonates with acids, crospovidone, sodium starch glycolate, agar, cation exchange resins, citrus pulp, veegum HV, natural sponge, and bentonite cross-linked polyvinylpyrrolidone, carboxymethyl starch, natural starch, microcrystalline cellulose, cellulose, gums, carboxymethylcellulose calcium, carboxymethylcellulose sodium, colloidal silicon dioxide, croscarmellose sodium, guar gum, polacrilin potassium, powdered cellulose, pregelatinized starch, sodium alginate, and sodium starch glycolate.

8. The antibiotic formulation of claim 1, in which the lubricant is at least one compound selected from the group consisting of magnesium stearate, calcium stearate, glyceryl monostearate, glyceryl palmitostearate, stearic acid, talc, and zinc stearate, stearic acid, magnesium lauryl sulfate, and colloidal silicon dioxide.

9. The synergistic antibiotic formulation of claim 1, in which the binder is at least one binder selected from the group consisting of acacia, sodium alginate, starch, gelatin, pregelatinized starch, partly pregelatinized starch, saccharides, glucose, sucrose, dextrose, lactose, molasses, extract of Irish moss, panwar gum, guar gum, ghatti gum, mucilage of isapol husk, carboxy methylcellulose, methylcellulose, veegur, larch arabolactan, polyethylene glycols, ethylcellulose, alcohols, waxes, and polyvinylpyrrolidone, hydroxypropylcellulose, hydroxypropylmethylcellulose, starch, gum arabic, dextrin and pullulan.

10. The antibiotic formulation of claim 1, in which the binder is Hydroxypropylmethyl cellulose of viscosity 50 cps.

11. The antibiotic formulation of claim 1, in which the formulation includes at least one surfactant selected from the group consisting of: sodium lauryl sulfate, sodium carboxy methyl cellulose, calcium carboxy methyl cellulose, hydrogenated or non-hydrogenated glycerolipids, ethoxylated or non-ethoxylated, linear or branched, saturated or mono- or polyunsaturated $C_6$ to $C_{30}$ fatty acids in the form of the acid or an alkali metal or its salt, cyclodextrin, sodium lauryl sulfate, alkaline earth metal or amine salt ethoxylated or non-ethoxylated esters of sucrose, sorbitol, sorbitan monooleate, mannitol, glycerol or polyglycerol containing from 2 to 20 glycerol units, or glycol with said fatty acids, mono-, di- or triglycerides or mixtures of glycerides of said fatty acids, ethoxylated or non-ethoxylated, linear or branched, saturated or mono- or polyunsaturated $C_6$ to $C_{30}$ fatty alcohols, cholesterol and derivatives thereof, other derivatives with a sterol skeleton, ethoxylated or non-ethoxylated ethers of sucrose, sorbitol, mannitol, glycerol or polyglycerol containing from 2 to 20 glycerol units, or glycol with said fatty alcohols, hydrogenated or non-hydrogenated, polyethoxylated vegetable oils, polyoxyethylene/polyoxypropylene block polymers (poloxamers), polyethylene glycol hydroxystearate, sphingolipids and sphingosine derivatives, polyalkyl glucosides, ceramides, polyethylene glycol/alkyl glycol copolymers, and polyethylene glycol/polyalkylene glycol ether di-block or tri-block copolymers, diacetylated monoglycerides, diethylene glycol monostearate, ethylene glycol monostearate, glyceryl monooleate, glyceryl monostearate, propylene glycol monostearate, macrogol stereate 400, macrogol stearate 2000, polyoxyethylene 50 stearate, macrogol ethers, cetomacrogol 1000, lauramacrogols, nonoxinols, octoxinols, tyloxapol, poloxamers, polysorbate 20, polysorbate 40, polysorbate 60, polysorbate 65, polysorbate 80, polysorbate 85, sorbitan monolaurate, sorbitan monooleate, sorbitan monopalmitate, sorbitan monostearate, sorbitan sesquioleate, sorbitan trioleate, sorbitan tristearate and sucrose esters.

12. The antibiotic formulation of claim 1, in which the excipient is one glidant of at least one member selected from the group consisting of: colloidal silicon dioxide, magnesium trisilicate, powdered cellulose, starch, talc and tribasic calcium phosphate, lactose, stearates, dibasic calcium phosphate, magnesium carbonate, magnesium oxide, calcium silicate, Cabosil, Sylold and silicon dioxide aerogels.

13. The antibiotic formulation of claim 1, in which the coating polymer is at least one polymer selected from the group consisting of: $C_{10}$-$C_{30}$ aliphatic acid, glycerides, wax, hydrogenated oil, cellulose containing polymers, stearic acid, palmitic acid, glyceryl ester aliphatic acid, glyceryl trilaurate, glyceryl trimyristate, glyceryl stearate, wax, paraffin, carnauba wax, spermaceti, beeswax, stearyl alcohol, cetostearyl alcohol, cottonseed oil, soyabean oils, polymethacrylate, polymethamethacrylate, ethyl cellulose, hydroxymethyl cellulose, hydroxymethyl propylcellulose; acid insoluble polymers; arabinogalactan; carboxymethylcellulose; gelatin; gum arabic; methylcellulose; polyvinyl alcohol; polyamide, and silicones; polyvinyl acetate, hydroxypropyl methylcellulose acetate, polyvinyl alcohol, maleic anhydride copolymers, .beta.-pinene polymers rosin, partially hydrogenated rosin and glycerol esters of rosin.

14. The antibiotic formulation of claim 1, in which the plasticizer in the coating is at least one plasticizer selected from the group consisting of: glycerol, polyethylene glycol, propylene glycol, sugar solution, alcohol, sorbitol, diethyl butyl pthalate, silicone, hexanol, pentanol, dimethylsulfoxide (DMSO), hexane, an oil, and mixtures thereof, oils, and mixtures thereof.

15. The antibiotic formulation of claim 1, which further includes at least one flavonoid added along with the cefixime trihydrate, said flavonoid selected from the group consisting of flavonoids containing quercetin, genistein, naringin, diosmin, acacetin and chrysin.

16. A process for making a antibiotic formulation of claim 1 comprising the steps of:
making a core by
i) mixing together Cloxacillin sodium 60 to 90% of the mass of the formulation;
Hydroxypropylmethyl cellulose 3 to 15% of the mass of the Cloxacillin sodium, a binder 1 to 6% of the mass of the Cloxacillin sodium and a solvent 15 to 45% of the mass of the Cloxacillin sodium, at speeds of 15 to 50 rpm to produce a sustained release homogenous mass;
ii) milling the homogenous mass through mesh sized ranging from 8 10 18 mm to obtain milled wet sustained release core particles;
iii) drying the milled core particles without heating for 10 to 20 minutes to obtain partially dried sustained release core particles;
iv) drying the partially dried sustained release core particles at temperatures ranging between 45 to 60 degrees Celsius for 30 to 60 minutes to obtain unsized dried sustained release core particles having moisture not more than 4%;
v) sifting and milling the dried core particles through mesh sizes ranging from 12 to 20 mesh to obtain sized dried sustained release core particles containing Cloxacillin sodium;
vi) vibrosifting together through a sifter having mesh size ranging from 30 to 40 mesh Cloxacillin sodium 10 to 40% of the mass of the total cloxacilin in the formulation; together with cefixime trihydrate 20 to 40% of the mass of Cloxacillin sodium; *lactobacillus sporogenes* being 0.5 to 4% mass of the Cloxacillin sodium; disintegrants being 1 to 5% of the mass of the Cloxacillin sodium to obtain vibrosifted immediate release particles;
vii) mixing together the sized dried sustained release core particles and the vibrosifted immediate release particles at temperatures below 25 degrees Celsius; at a relative humidity of less than 60 percent for 20 to 30 minutes at 20 to 500 rpm;
viii) adding to the mixture excipients including lubricants 1 to 5% mass of the Cloxacillin sodium and further mixing for 3 to 5 minutes to obtain core particles;
ix) compressing the core particles at temperatures below 25 degrees Celsius; at a relative humidity of less than 60 percent at compression pressures ranging from 1 kg/sq cm to 12 kg/sq cm to obtain cores of the antibiotic formulation;
and enveloping the said cores with a coating consisting of a coating polymer having mass 1 to 3% of the mass of the core; a solvent for dissolving the polymer having a mass of 5 to 45% of the mass of the core; a plasticizer having a mass of 0.05 to 2% of the mass of the core; and a coloring agent having a mass of 0.05% to 5% of the mass of the core in a coating machine at temperatures ranging from 40 to 60 degrees Celsius to obtain the synergistic antibiotic formulation.

17. A process for making a antibiotic formulation comprising the steps of:
making a core by
i) mixing together Cloxacillin sodium 60 to 90% of the mass of the total cloxacillin in the formulation;
Hydroxypropylmethyl cellulose 3 to 15% of the mass of the Cloxacillin sodium, a binder 1 to 6% of the mass of the Cloxacillin sodium and a solvent 5 to 45% of the mass of the Cloxacillin sodium, at speeds of 15 to 50 rpm to produce a sustained release homogenous mass;

ii) milling the homogenous mass through mesh sizes ranging from 8 to 18 mm to obtain milled wet sustained release core particles;

iii) drying the milled core particles without heating for 10 to 20 minutes to obtain partially dried sustained release core particles;

iv) drying the partially dried sustained release core particles at temperatures ranging between 45 to 60 degrees Celsius for 30 to 60 minutes to obtain unsized dried sustained release core particles having moisture not more than 4%;

v) sifting and milling the dried core particles through mesh sizes ranging from 12 to 20 mesh to obtain sized dried sustained release core particles containing Cloxacillin sodium;

vi) vibrosifting together through a sifter having mesh size ranging from 30 to 40 mesh Cloxacillin sodium 10 to 40% of the mass of the total cloxaxillin in the formulation; together with cefixime trihydrate 20 to 40% of the mass of Cloxacillin Sodium;

*lactobacillus sporogenes* being 0.5 to 4% mass of the Cloxacillin sodium; disintegrants being 1 to 5% of the mass of the Cloxacillin sodium; glidants having mass between 1 to 6% of the Cloxacillin sodium and surfactants having mass between 1 to 5% of the Cloxacillin sodium to obtain vibrosifted immediate release particles;

vii) mixing together the sized dried sustained release core particles and the vibrosifted immediate release particles at temperatures below 25 degrees Celsius; at a relative humidity of less than 60 percent for 20 to 30 minutes at 20 to 500 rpm;

viii) adding to the mixture excipients including lubricants 1 to 5% mass of the Cloxacillin sodium and further mixing for 3 to 5 minutes to obtain core particles;

ix) compressing the core particles at temperatures below 25 degrees Celsius; at a relative humidity of less than 60 percent at compression pressures ranging from 1 kg/sq cm to 12 kg/sq cm to obtain cores of the antibiotic formulation and enveloping the said cores with a coating consisting of a coating polymer having mass 1 to 3% of the mass of the core; a solvent for dissolving the polymer having a mass of 0.05 to 2% of the mass of the core; and a coloring agent having a mass of 0.05 to 2% of the mass of the core in a coating machine at temperatures ranging from 40 to 60 degrees Celsius to obtain the synergistic antibiotic formulation.

18. A process for making a antibiotic formulation as claimed in claim 17, which includes the step of dispersing at least one flavonoid in the cefixime trihydrate at the time of vibrosifting step.

* * * * *